United States Patent [19]

Sugimoto

[11] Patent Number: 4,621,053
[45] Date of Patent: * Nov. 4, 1986

[54] PROCESS FOR THE PRODUCTION OF HUMAN PEPTIDE HORMONES

[75] Inventor: Kaname Sugimoto, Okayama, Japan

[73] Assignee: Kabushiki Kaisha Hayashibara Seibutsu Kagaku Kenkyujo, Okayama, Japan

[*] Notice: The portion of the term of this patent subsequent to May 10, 2000 has been disclaimed.

[21] Appl. No.: 584,017

[22] Filed: Feb. 27, 1984

Related U.S. Application Data

[63] Continuation-in-part of Ser. No. 281,941, Jul. 10, 1981, abandoned, Ser. No. 281,942, Jul. 10, 1981, abandoned, Ser. No. 290,864, Aug. 7, 1981, abandoned, Ser. No. 322,184, Nov. 17, 1981, abandoned, Ser. No. 325,033, Nov. 25, 1981, abandoned, Ser. No. 329,116, Dec. 9, 1981, abandoned, Ser. No. 329,117, Dec. 9, 1981, abandoned, and Ser. No. 329,120, Dec. 9, 1981, abandoned.

[30] Foreign Application Priority Data

| Jul. 30, 1980 | [JP] | Japan | 55-104726 |
| Jul. 31, 1980 | [JP] | Japan | 55-105273 |
| Aug. 22, 1980 | [JP] | Japan | 55-114680 |
| Dec. 13, 1980 | [JP] | Japan | 55-176185 |
| Dec. 19, 1980 | [JP] | Japan | 55-180241 |
| Dec. 30, 1980 | [JP] | Japan | 55-187012 |
| Dec. 30, 1980 | [JP] | Japan | 55-187811 |
| Dec. 30, 1980 | [JP] | Japan | 55-187010 |

[51] Int. Cl.$^4$ .............. C12P 21/00; C12N 15/00; C12N 5/00; C12N 5/02
[52] U.S. Cl. .............. 435/68; 435/172.2; 435/240; 435/241; 435/284; 435/948; 530/399; 935/106; 935/109
[58] Field of Search .............. 435/68, 172.2, 240, 435/241, 284–286; 424/85, 86, 87; 935/89, 99, 93, 109, 106; 436/548; 260/112 B, 112 R; 530/399

[56] References Cited

U.S. PATENT DOCUMENTS

| 3,886,132 | 5/1975 | Brewer et al. | 424/177 |
| 4,195,125 | 3/1980 | Wacker | 435/71 |
| 4,225,671 | 9/1980 | Puchinger et al. | 435/71 |
| 4,242,460 | 12/1980 | Chick et al. | 435/284 |
| 4,276,282 | 6/1981 | Sugimoto et al. | |
| 4,285,929 | 8/1981 | Sugimoto et al. | 435/68 |
| 4,328,207 | 5/1982 | Sugimoto | |
| 4,352,883 | 10/1982 | Lim | 435/240 |
| 4,377,513 | 3/1983 | Sugimoto | |
| 4,383,034 | 5/1983 | Sugimoto et al. | |
| 4,383,035 | 5/1983 | Sugimoto et al. | |
| 4,383,036 | 5/1983 | Sugimoto et al. | |

OTHER PUBLICATIONS

Pattillo, "Hormone Synthesis and Function in vitro", *Growth, Nutrition and Metabolism of Cells in Culture*, 225–227 (1972) Academic Press, N.Y.
Bordelon, M. R., et al, "Human Glycoprotein Hormone Production in Human-Human and Human-Mouse Somatic Cell Hybrids", *Exp. Cell Research*, 103 (1976) 303–310.
Lewin, *Gene Expression*, vol. 2, 259–265 (1980) John Wiley and Sons, New York.
Zeleznik, "Production of Long Term Steroid-Producing Granulosa Cell Cultures by Cell Hybridozation", *Endocrinology*, vol. 105, pp. 156–162 (1979).
Mashiter et al, "Hormone Secretion by Human Somatotrophic, Lactotrophic and Mixt Pituitary Adenomas in Culture", *J. Clin. Endo. and Met.*, vol. 48, pp. 108–113 (1979).
Thompson, J. S. et al, "Heterologous Transplantation of Mouse Tumors into the Newborn Albino Rat", *Cancer Research*, vol. 20, pp. 1365–1371 (1960).
Sato, J., "The Current Stimulation of the Maintenance and Preservation of Tissue Culture Cell Lines in Japan", *Protein, Nucleic Acid and Enzyme*, vol. 20, pp. 616–643 (1975).
Hwang, P. et al, "A Radioimmunoassay for Human Prolactin", *Por. Nat. Acad. Sci. USA.*, vol. 68, #8, pp. 1902–1906 (1971).
Glick, S. M. et al, "Immunoassay of Human Growth Hormone in Plasma", *Nature*, vol. 199, pp. 784–787 (1963).
Bertagna et al, "Characterization of Materials Secreter in vitro by a Human Pituitary Adenoma", *J. of Clin. Endo. and Met.*, vol. 49, pp. 527–532 (1979).
Owerbach et al. "Genes for Growth Hormone, Chorionic Somatomammotropin and Growth Hormone–Like Gene", *Science*, vol. 206, (Jul. 1980).
Midgley, Jr. A. R., "Radioimmunoassay: A Method for Human Chorionic and Human Luteinizing Hormone", *Endocrinology*, vol. 79, pp. 10–18 (1966).
Gagel, R. F. et al, "Establishment of a Calcitonin-Producing Rat Medullary Thyroid Carcinoma Cell Line. II. Secretory Studies of the Tumor and Cells in Culture", *Endoctrinology*, 170, pp. 516–523 (1980).

(List continued on next page.)

*Primary Examiner*—Sidney Marantz
*Assistant Examiner*—Patricia L. DeSantis
*Attorney, Agent, or Firm*—Browdy and Neimark

[57] ABSTRACT

Human peptide hormones, such as insulin, growth hormone, prolactin, adrenocorticotropic hormone, placental lactogen, calcitonin, parathyroid hormone and thyroid stimulating hormone, are produced by implanting a human×human hybridoma lymphoblastoid cell line capable of producing the human peptide hormone in a non-human warm-blooded animal. After a period of time, the resultant tumor is extracted and disaggregated and then cultured in vitro under conditions appropriate to accumulate the human peptide hormone. The human-×human hybridoma lymphoblastoid cell line is preferably formed by fusing parent human cells inherently capable of producing the human peptide hormone with a human lymphoblastoid line, preferably of leukemic origin. This process permits a substantial increase in the amount of human peptide hormone which can be produced.

58 Claims, No Drawings

OTHER PUBLICATIONS

Bertagna, X. Y., et al, "Excopic Production of High Molecular Weight Calcitonin and Corticotropin by Human Small Cell Carcinoma Cells in Tissue Culture: Evidence for Separate Precursors", *J. Clin. Endo. and Methabolism*, 47, 1390–1393 (1980).

Chemical Abstracts, 96: 179463k (1982).

Shin, "Use of Nude Mice for Tumorigenicity Testing and Mass Propagation", *Methods in Enzymology*, vol. LVIII, pp. 370–379 (1979).

Sekiguchi, M., "List of Human Cancer Cell Lines Established in Japan", *The Tissue Culture*, vol. 6, No. 13, pp. 527–546 (1980).

Amino, N. et al, "Human Lymphotoxin Obtained from Established Lymphoid Lines; Purification Characteristics and Inhibition by Anti-Immunoglobulin", *The Journal of Immunology*, vol. 113, No. 4, pp. 1134–1345 (1974).

Miyoshi, I. et al, "Establishment of an Epstein-Barr Virus-Negative B-Cell Lymphoma Line from a Japanese Burkitt's Lymphoma and Its Serial Passage in Hamsters", *Cancer*, vol. 40, pp. 2999–3003 (1977).

Miyoshi, I. et al, "Human B Cell, T Cell and Null Cell Leukaemic Cell Lines Derived from Acute Lymphoblastic lekuaemias", *Nature*, vol. 267, No. 4614, pp. 843–844.

American Type Culture Collection, Catalogue of Strains II, Fourth Edition, 1983, pp. 139, 144.

PROCESS FOR THE PRODUCTION OF HUMAN PEPTIDE HORMONES

CROSS REFERENCE TO RELATED APPLICATIONS

The present application is a continuation-in-part of each of the following copending applications, the entire contents of each of which are hereby incorporated herein by reference: Ser. No. 281,941, filed July 10, 1981, now abandoned; Ser. No. 281,942, filed July 10, 1981, now abandoned; Ser. No. 290,864, filed Aug. 7, 1981, now abandoned; Ser. No. 322,184, filed Nov. 17, 1981, now abandoned; Ser. No. 325,033, filed Nov. 25, 1981, now abandoned; Ser. No. 329,116, filed Dec. 9, 1981, now abandoned; Ser. No. 329,117, filed Dec. 9, 1981, now abandoned; and Ser. No. 329,120, filed Dec. 9, 1981, now abandoned.

The following patents of the same inventor are related to the present application: U.S. Pat. Nos. 4,383,034, 4,383,035, 4,383,036. U.S. Pat. No. 4,377,513, of which the present inventor is a coinventor, is also related to the present application.

FIELD OF THE INVENTION

The present invention relates to a process for producing human peptide hormones, such as insulin, growth hormone (hGH), prolactin, adrenocorticotropic hormone (hACTH), placental lactogen (hPL), calcitonin (hCT), parathyroid hormone (hPTH), and thyroid stimulating hormone (hTSH).

DESCRIPTION OF THE PRIOR ART

All peptide hormones produced in the human body exert a physiological effect on the individual. Various undesirable diseases and conditions occur when there is a deficiency in any given peptide hormone. Accordingly, means to mass-produce such peptide hormones have been long sought so that they may be used in the treatment of such diseases or conditions.

While various of the peptide hormones produced in the human find their counterparts produced in animals, and are usually non-species-specific, it is less desirable to use such peptide hormones of animal origin as opposed to the corresponding peptide hormones of human origin. There is a particular risk as to antigen-antibody reaction of peptide hormones derived from animals when used as therapeutic agents for humans, as opposed to the corresponding peptide hormones from viable human cells.

All of these peptide hormones have been separated, in the laboratory, from the cells which naturally produce them and have been studied. It has not previously been posible to produce sufficient peptide hormone from the in vitro culturing of such human cells to serve therapeutic purposes. The techniques of chemical synthesis or cultivation of genetically recombined microorganisms have also been attempted, but the processes generally result in low yield and high production cost. Some of these peptide hormones, such as hACTH, can be recovered from human urine and others ay be recovered from human serum. However, these are expensive processes and the supply of starting product is limited.

Among the peptide hormones for therapeutic utility for which means of mass production have been particularly sought, are human growth hormone, human insulin, human prolactin, human adrenocorticotropic hormone, human placental lactogen, human calcitonin, human parathyroid hormone, and human thyroid stimulating hormone.

Human growth hormone is presently in commercial use as a therapeutic agent. It has been produced by processes such as chemical synthesis, in vitro tissue culture or cultivation of genetically recombined microorganisms, but all of these processes result in very low hGH yield and high production cost.

Human insulin is, of course, in general use for the treatment of diabetes. As is the case with human growth hormone, while production of human insulin has been attempted by means of chemical synthesis, in vitro tissue culture, and cultivation of genetically recombined microorganisms, these processes have resulted in a very low human insulin yield and high production cost. Accordingly, insulin from bovine or porcine sources has been utilized for therapeutic purposes in the past. A high yield - low cost method for producing human insulin is in great demand.

Human prolactin, also known as lactogenic hormone, is a protein secreted by human acidophile adenoma cells of the anterior pituitary which stimulates the growth of mammary gland, prostate and seminal vesicles. The compound has therapeutic utility in causing the stimulation of lactation. No process for the mass production of human prolactin has yet been established.

Human adrenocorticotropic hormone, also known as adrenocorticotropin, is a polypeptide secreted by the anterior pituitary and has therapeutic utility in stimulating the adrenocortex to produce cortical hormones. It may be isolated from pituitaries or from female human urine, but no means of mass production of this hormone is yet known.

Human placental lactogen, also known as human chorionic somatomammotropin, is a polypeptide secreted by the human syncytiotrophoblast of the chorionic villi in the human placenta. This hormone has many physiochemical and immunological similarities to hGH. It has some metabolic effects which are qualitatively similar to those of growth hormone, including inhibition of glucose uptake, stimulation of free fatty acid and glycerol release, enhancement of nitrogen and calcium retention (despite increased urinary calcium excretion), reduction in the urinary excretion of phosphorus and potassium, and an increase in the turnover of hydroxyproline, as reflected by increased urinary excretion of that amino acid. No process for the mass production of low cost human placental lactogen has yet been established.

Human calcitonin is a peptide secreted by human parafollicular cells in the thyroid gland which suppresses the release of calcium from bones into the blood, and also the secretion of insulin. Again, no effective process to produce a large amount of human calcitonin at low cost has heretofore been established.

Human parathyroid hormone, also known as parathormone, is a hormone secreted by the parathyroid gland that regulates the synthesis of activated vitamin $D_3$, stimulates the release of calcium from bone, and leads to an increase in the blood level of calcium. As with the other hormones discussed, no process for the mass production of low cost human parathyroid hormone has yet been established.

Human thyroid stimulating hormone, also known as human thyrotropin, is a glycoprotein secreted by the pituitary gland which stimulates the growth of the thyroid gland and the intake of iodine into other human hormones. It further activates ATPase. The mass production of low cost human thyroid stimulating hormone has also been long sought.

The present inventor is the inventor or co-inventor of prior U.S. Pat. Nos. 4,276,282, 4,285,929 and 4,328,207. U.S. Pat. No. 4,276,282 is drawn to a process for the production of human interferon (HuIFN), while U.S. Pat. No. 4,285,929 is drawn to a similar process for the specific production of human Type II interferon (HuIFN-γ). The U.S. Pat. No. 4,328,207 is drawn to a related process for the production of mouse interferon (MuIFN). The processes disclosed in the first two of these patents comprise multiplying an established human cell line by transplanting it into a non-human warm-blooded animal body, or into a diffusion chamber through which the nutrient body fluids of the animal passes, in which multiplication of the transplanted cells takes place. The multiplied cells are then exposed to an interferon inducer, either in vivo or in vitro to induce the production of interferon, and the interferon produced is then purified and separated from the cells. These patents disclose that by growing a human lymphoblastoid line in or on a non-human warm-blooded animal, it multiplies more stably and rapidly to obtain a larger production of cells than can be obtained in -vitro, and to unexpectedly obtain a higher interferon yield per cell than is obtainable when the cells are multiplied in vitro. U.S. Pat. No. 4,328,207 discloses a similar process for producing mouse interferon.

Human interferon is not a peptide hormone. It is produced only in extremely minute quantities, and then only after being induced by an interferon inducing agent. In addition, IFNs are strongly species-specific while peptide hormones are substantially non-species-specific. The fact that the yield of human interferon per cell can be increased by first multiplying a human lymphoblastoid cell line in or on a non-human warm-blooded animal would not make obvious the subsequent discovery by the present inventor that all human peptide hormones can be mass-produced by first fusing parent human cells inherently capable of producing the human peptide hormone with a human lumphoblastoid line and then multiplying the obtained hybridoma line in or on a non-human warm-blooded animal, obtaining in every case a higher yield of the substance being produced per milliliter of cell suspension that obtainable from in vitro production. The prior Sugimoto interferon patents disclose nothing whatsoever about the use of hybridomas, nor does the experience with interferon make obvious the results obtained with human peptide hormones.

SUMMARY OF THE INVENTION

Accordingly, it is an object of the present invention to eliminate the deficiencies of the prior art as discussed hereinabove.

It is a further object of the present invention to provide a process for the low cost mass production of human peptide hormones.

It is another object of the present invention to provide a process for obtaining hybridoma cells capable of human peptide hormone production higher than that of the parent cells used to obtain the hybridoma.

It is still another object of the present invention to provide a process to augment the per cell human peptide hormone production of cell lines capable of producing such a human peptide hormone.

It is another object of the present invention to provide an efficient process for multiplying human hybridoma cells capable of producing human peptide hormones.

It is yet a further object of the present invention to provide a process for producing high titered human peptide hormones with the human hybridoma cells thus obtained.

It is still another object of the present invention to provide a process for the low cost mass production of human growth hormone.

It is still another object of the present invention to provide a process for the low cost mass production of human insulin.

It is still another object of the present invention to provide a process for the low cost mass production of human prolactin.

It is still another object of the present invention to provide a process for the low cost mass production of human adrenocorticotropic hormone.

It is still another object of the present invention to provide a process for the low cost mass production of human placental lactogen.

It is still another object of the present invention to provide a process for the low cost mass production of human calcitonin.

It is still another object of the present invention to provide a process for the low cost mass production of human parathyroid hormone.

It is still another object of the present invention to provide a process for the low cost mass production of human thyroid stimulating hormone.

Broadly, these and other objects, as may become apparent hereinafter, have been obtained by the process which comprises multiplying a human lymphoblastoid line capable of producing the specific desired human peptide hormone by transplanting said cell line to a non-human warm-blooded animal or, alternatively, allowing said cell line to multiply in a conventional-type diffusion chamber by which the nutrient body fluid of a non-human warm-blooded animal is supplied to the cell line. The human peptide hormone is then produced with the human cells multiplied by either of the above in vivo multiplication procedures.

More particularly, these and other objects as may become apparent have been obtained by the process comprising either (1) implanting the human cell line capable of producing the desired human peptide hormone to a non-human warm-blooded animal; feeding the animal to allow the human cell line to utilize the nutrient body fluids supplied from the animal for their multiplication; extracting and disaggregating the resultant tumor, formed in the animal, to obtain the multiplied human cells; culturing the human cells in an in vitro nutrient medium for a period sufficient to accumulate a significant amount of the desired human peptide hormone; and recovering the accumulated human peptide hormone from the culture, or alternatively, (2) placing a suspension of such human cell line in a conventional type diffusion chamber by which the nutrient body fluid of a non-human warm-blooded animal is supplied to the human cell line; embedding or placing the chamber in or on the non-human warm-blooded animal feeding the animal to allow the human cell to utilize the nutrient body fluid supplied for their multiplication; and then collecting and culturing the cells in vitro and recovering the accumulated human peptide hormone as described in the first alternative procedure.

The feature of the present invention which allows even greater multiplication of the human cells and larger production of the desired human peptide hormone, comprises using as the human cells which are implanted into the non-human warm-blooded animal, or into the diffusion chamber, a human×human hybridoma line which comprises a human lymphoblastoid line in which the genes coded for the production of the desired peptide hormone have been introduced by a suitable technique. The use of such a hybridoma line results in an extreme increase in cell multiplication rate and human peptide hormone production per cell, i.e. about 2-10-fold higher than that obtained by means of the process of the present invention using non-hybridoma cells productive of the human peptide hormone.

DETAILED DESCRIPTION OF PREFERRED EMBODIMENTS

The outstanding increase in human peptide hormone production obtainable by means of the present invention is made possible due to the combination of two discoveries by the present inventor. The first is that the rate of cell multiplication and the amount of human peptide hormone obtainable per cell from a cell line which is otherwise capable of producing the human peptide hormone in question, can be greatly increased by first multiplying the cell line in or on a non-human warm-blooded animal, i.e. by either implanting the cells directly into the animal, or by growing them in a diffusion chamber which is attached to the animal so as to allow the nutrient body fluids of the living animal to be supplied to the cells.

The second discovery is that human cells inherently capable of producing the human peptide hormone in question, can be fused to a human lymphoblastoid cell line, preferably of leukemic origin, in order to obtain a faster growing cell line with increased human peptide hormone productivity.

The combination of these discoveries synergistically provided the result that when such hybridoma cells are multiplied in or on a non-human warm-blooded animal, the productivity of human peptide hormone per cell increases to such a large extent that it could not be predictable either from the productivity of the hybridoma in vitro or from the productivity of the parent hormone-producing cell line multiplied in or on a non-human warm-blooded animal.

The human×human hybridoma cell line which is used in accordance with the present invention, may conveniently be obtained by any of the techniques of cell fusion which may be known to the art. References which disclose methods of cell fusion include Yamanaka, T. et al, *Biken Journal,* vol. 9, pp. 159–175 (1966), or Pontecorvo, G., *Somatic Cell Genet.,* Vol. 1, No. 4, pp. 397–400 (October 1975), the contents of which are hereby incorporated by reference. The parent human cells inherently capable of producing a human peptide hormone may be fused with a human lymphoblastoid line, preferably of leukemic origin, by suspending the parent human cells together with the human lymphoblastoid line in a salt solution containing an effective amount of a cell fusion inducing agent and allowing the resultant cell suspension to stand for a period of time sufficient to effect the cell fusion. The hybridoma lines obtained are then tested for human peptide hormone producibility. Those having a higher human peptide hormone producibility than that of the parent human cells are selected and cloned. It is these lines which will have a great increase in human peptide hormone producibility after being allowed to multiply in or on a non-human warm-blooded animal.

The fusion inducing agent which may be used in this process may be any agent which will induce cell fusion, preferably Sendai virus or polyethylene glycol.

Implantation of such a human×human hybridoma lymphoblastoid line into the animal body results in the formation of a massive tumor which is not contaminated in any substantial way with host animal cells. The massive tumors are easily disaggregatable and can thus be easily harvested. Such human×human hybridoma lymphoblastoid lines also reproduce very rapidly in a diffusion chamber attached to a non-human warm-blooded animal in such a manner that the nutrient body fluids of the animal is permitted to contact the cells within the chamber.

As long as the "hybridoma" cell line is basically a lymphoblastoid line, preferably of leukemic origin, which contains the genes governing the production of the human peptide hormone in question, it may be used in the process of the present invention. For example, the human peptide hormone production governing genes may be introduced into the lymphoblastoid line, preferably of leukemic origin, by means of genetic engineering techniques, such as recombinant DNA techniques, using enzymes such as DNA ligase, nuclease, and DNA polymerase. Thus, the term "human×human hybridoma lymphoblastoid line capable of producing human peptide hormone" as used throughout the present specification and claims is intended to include not only lymphoblastoid lines produced by cell fusion between parent human cells inherently capable of producing the human peptide hormone and the human lymphoblastoid line, but also to human lymphoblastoid lines which have been altered in any manner, such as by genetic engineering, so as to be capable of producing human peptide hormone.

The human lymphoblastoid line, into which the human peptide hormone-producing ability is introduced in order to obtain the human human hybridoma line used in the process of the present invention, may be any lymphoblastoid line of human origin which forms a tumor implanted in an immuno-deficient or immuno-suppressed non-human warm-blooded animal. Such human lymphoblastoid lines are obtainable by establishing in a suitable manner lymphoblastoid cells from a patient suffering from a leukemia, e.g. acute lymphatic leukemia, acute myelogeneous leukemia or chronic myelogenous leukemia, malignant lymphoma, Burkitt lymphoma or infectious mononucleosis. Human lymphoblastoid lines usable in the present invention may also be obtained by transforming normal human lymphocytes by use of a suitable carcinogenic virus, agent or irradiation, such as Epstein-Barr virus (EB virus), mitogen or x-ray irradiation, and establishing the obtained lymphoblastoid cells. Examples of such lines are B-Ta, Q-Ta, B-Ue, Q-Ue, B-Ke, and Q-Ku, reported in Sato, J., *Protein, Nucleic Acid and Enzyme,* 20, 6, 616–643 (1975). Preferably, the human lymphoblastoid line is of leukemic origin as, for example, Namalva, reported by Strander, H. et al, *Journal of Microbiology,* 1, 116–117 (1975), BALL-1, TALL-1, or NALL-1, reported by Miyoshi, I. et al, *Nature,* 267, 4614, 843–844 (1977), or JBL, reported by Miyoshi, I. et al, *Cancer,* 40, 2999–3003 (1977). Other lymphoblastoid cell lines usable include the other human lymphoblastoid cell lines listed in the above cited Strander et al publication, including Akuba, PeHR-1 and LY-46. Others include the cell lines M-7002 and B-7101 as described in *Journal of Immunology*, 113, 1334–1345 (1974); EBV-Sa, EBV-Wa, MOLT-3 and EBV-HO, as described in *The Tissue Culture*, 6, 13, 527–536 (1980); CCRF-SB (ATCC CCL 120); BALM 2, DND-41; etc.

While these cell lines are specifically mentioned, it should be understood that any lymphoblastoid line which forms a tumor after being implanted in an immuno-deficient or immuno-suppressed non-human warm-blooded animal may be used in accordance with the present invention.

The human parent cells which are fused with the lymphoblastoid cell line, in order to obtain the human-×human hybridoma line used in the present invention, may be any human cell which inherently produces the human peptide hormone to be produced. For example, in the case of hGH, the cells may be intact human acidophile cells from the anterior pituitary or such cells which have first been transformed with EB virus or x-ray irradiation. Also usable are acidophile adenoma cells from a patient suffering from acidophile adenoma of the pituitary gland, or human lung carcinoma cells which produce ectopic hGH.

In the case of human insulin, cells may be intact human pancreas Langerhans island β-cells, or such cells which have first been transformed by EB virus or x-ray irradiation. Also usable are insuloma cells from patients suffering from insuloma, or human lung carcinoma cells which produce ectopic human insulin.

In the case of prolactin, the cells may be intact human acidophile cells from the anterior pituitary, or such cells which have first been transformed with EB virus or x-ray irradiation. Also usable are acidophile adenoma cells from a patient suffering from acidophile adenoma of the pituitary gland, or human lung carcinoma cells which produce ectopic human prolactin.

For hACTH, the cells may be those from the anterior lobe of the pituitary gland, pituitary tumor cells or chromophobe adenoma cells. Also usable are other human cells which produce ectopic hACTH such as pancreas carcinoma cells from Langerhans island or lung carcinoma cells.

In the case of placental lactogen, the cells may be syncytiotrophoblast cells of the chorionic villi, or chorionic epithelioma cells. Also usable are lung carcinoma cells which produce ectopic hPL.

In the case of hCT. the cells may be human parafollicular cells from the thyroid gland or thyroidea adenoma cells. Also usable are human tumor cells capable of producing ectopic hCT, such as human carcinoid cells or human lung tumor cells.

In the case of hPTH, cells may be normal or transformed parathyroid cells, or cells which produce ectopic hPTH, such as lung carcinoma cells, ovarian tumor cells, kidney carcinoma cells, or liver carcinoma cells.

In the case of hTSH, cells may be basophile cells from the anterior lobe of the pituitary gland, pituitary tumor cells, or chromophobe adenoma cells from the pituitary gland. Also usable are human cells which produce ectopic hTSH, such as lung carcinoma cells.

The above list is not intended to be complete, and any cell line which inherently produces the human peptide hormone being sought may be used as the parent cells which are fused with the lymphoblastoid cell line to obtain the human×human hybridoma used in accordance with the present invention.

The human×human hybridoma cells which are capable of producing human peptide hormone may be directly implanted into, or inserted into a diffusion chamber which is connected to any non-human warm-blooded animal which will support cell multiplication. Examples of usable animals include poultry, such as chickens and pigeons, or mammalians, such as dogs, cats, monkeys, goats, pigs, cows. horses, rabbits, guinea pigs, rats, hamsters, mice, and nude mice.

Since direct cell implantation often elicits undesirable immuno-reaction, the use of immuno-deficient or immuno-suppressed animals is preferable. Examples of immuno-deficient animals are newborn or infant animals, or those in the youngest possible stage, for example, the use of eggs, embryos, or fetuses is desirable. Since the nude mouse, when used as the non-human warm-blooded animal, exhibits weaker immuno-reaction, even when in its adulthood, they may be used directly as the immuno-deficient animal without need of any immuno-suppression. Alternatively, immune reaction may be suppressed prior to cell implantation by treatment of the animal with x-ray or γ-ray irradiation, for example about 200–600 rem, or injection of antiserum or immuno-suppressive agent prepared according to conventional methods.

When the diffusion chamber embodiment of the present invention is used, since no immuno-reaction is elicited due to the absence of direct contact of the hybridoma cells with the host animal cells, any non-human warm-blooded animal can be used without any pretreatment to suppress immuno-reaction.

A particularly advantageous method to stabilize cell multiplication and augment human peptide hormone production involves repeated transplantation, using a combination or combinations of different non-human warm-blooded animals. For example, the hybridoma cells may first be implanted into a hamster and multiplied therein, and then re-implanted in a nude mouse. The repeated transplantation may be carried out with animals of different species within the same class or division, as well as with those of the same species or genus.

The hybridoma cells can be implanted at any site of the animal, as long as the cells multiply thereat. For example, the cells may be implanted in the allantoic cavity or intravenously, intraperitoneally or subcutaneously.

Besides direct implantation of the cells into the animal body hybridoma cell lines may be multiplied while utilizing the nutrient body fluids supplied from the non-human warm-blooded animal through the use of a conventional diffusion chamber of any of various shapes and sizes. The diffusion chamber may be imbedded with a porous membrane filter, ultra-filter, or hollow fiber with pore sizes of about $10^{-7}$ to $10^{-5}$ m in diameter, which prevents contamination of the hybridoma cells with host cells within the diffusion chamber, yet allows the animal to supply the cells with its nutrient body fluid.

The diffusion chamber may be imbedded, for example, intraperitoneally, in the animal body, or it can be designed to be placed on the exterior of the host animal while being connected to the blood stream of the animal so as to permit the body fluid of the animal to circulate into the chamber. Placing the diffusion chamber on the exterior of the animal allows the advantages of enabling observation of the cell suspension in the chamber through a transparent side window equipped on the chamber wall, and also enables replacement and exchange with a fresh chamber. Cell multiplication thereby increases to a further higher level over the period of the animal's life, and the cell production per animal is further augmented without any sacrifice of the host animal. The multiplied human cells may be harvested easily without contamination by the animal's cells when using the diffusion chamber embodiment. Furthermore, the same improvement of productivity per cell of the cell line is achieved when using the diffusion chamber embodiment as when using the direct implantation embodiment.

Feeding of the host animal which has been implanted with the human cells, or which carries the diffusion chamber, may be carried out easily by conventional methods, and no special care is required. Maximum cell multiplication is obtained within 1–5 weeks after the cell implantation or the attachment of the diffusion chamber. The number of human cells obtained per host ranges from about $10^7$ to $10^{12}$ or more. In other words, the number of human cells transplanted in the animal body increases about $10^2$ to $10^7$-fold or more, or about $10^6$-fold more than that obtained by in vitro tissue culture methods.

After the hybridoma cells are multiplied in or on the non-human warm-blooded animal, they are collected and cultivated in vitro by an appropriate nutrient medium under conditions appropriate to accumulate a substantial amount of the peptide hormone in a manner well known per se. For example, the human×human hybridoma lymphoblastoid cells obtained after removal from the diffusion chamber or from suspension in acites, or after extracting and disaggregating the massive tumor formed subcutaneously, are su pended to give a cell concentration of about $10^4$ to $10^8$ cells per milliliter in a nutrient medium, pre-warmed at a temperature of about 20° to 40° C., and then incubated at this temperature for 1–50 hours to produce the human peptide hormone.

In some cases, it is necessary to subject the cells being so incubated in vitro to an inducer in order to cause the hormone to be released or to an agent for enhancing the hormone production. For example, the production of hGH, human insulin, human prolactin and hACTH usually must be induced by an appropriate inducing agent In the case of hGH the cells being incubated at the temperature of 20° to 40° C. are subjected to a growth hormone inducer at this temperature for about 1–20 hours to induce hGH. Preferable growth hormone inducers are amino acids, such as glycine, arginine, tryptophan, leucine, casamino acid and L-DOPA, amino acid metabolites, such as seratonin, and peptides.

In the case of insulin, the cells being incubated at 20° to 40° C. may be subjected to an insulin inducer at this temperature for about 1 to 20 hours to induce human insulin. Preferable insulin inducers are saccharides, such as glucose, mannose, fructose, ribose and xylitol; amino acids such as arginine, lyscine and leucine; peptide hormones, such as glucagon and adrenocorticotropic hormone (ACTH); and metal cations, such as $K^+$ and $Ca^{++}$.

Prolactin productive cells may be subjected to a prolactin inducer while incubating at a temperature of about 20° to 40° C. for about 1 to 50 hours to induce human prolactin. Preferable prolactin inducers are organic compounds such as reserpin, phenothiazine or chlorpromazine; hormones such as thyrotropin-releasing hormone and estrogen; amino acids such as lysine, arginine and cysteine; and inorganic salts such as sodium chloride, potassium chloride, calcium chloride and magnesium sulfate.

The cells productive of hACTH are subjected to an adrenocorticotropic hormone inducer while being incubated at an temperature of about 20° to 40° C. for about 1 to 50 hours to induce hACTH. Preferable adrenocorticotropic inducers usable in the present invention are vasopressin, atropine methyl nitrate, insulin, glucagon, bacterial endotoxin, seratonin and propranolol.

Even if the use of inducer is not necessary in order to cause the cells to produce the peptide hormone, oftentimes the production can be enhanced by the use of certain known agents for this purpose. For example, production of hPL may be enhanced by carrying out the incubation in the presence of one or more amino acids such as leucine, lysine, arginine and cysteine; inorganic salts, such as sodium chloride, potassium chloride, calcium chloride and magnesium sulfate; or hormones, such as luteinizing hormone releasing hormone.

Human calcitonin producion enhancing agents are known to include amino acids, such as glycine, leucine, lysine, arginine and cysteine; inorganic salts, such as sodium chloride, postassium chloride, calcium chloride and magnesium sulfate; and hormones, such as dibutyl-cyclic AMP and prostaglandin E.

In the case of hPTH, the production may be enhanced if the incubation is carried out in the presence of amino acids, such as glycine, leucine, lysine, arginine, or cysteine; inorganic salts, such as sodium chloride, potassium chloride, calcium chloride and magnesium sulfate; or hormones, such as dopamine, isoproterenol, epinephrine and norepinephrine.

Enhancement of hTSH production may be obtained by carrying out the incubation in the presence of amino acids, such as glycine, leucine, lysine, arginine, or cysteine; inorganic salts, such as sodium chloride, potassium chloride, calcium chloride and magnesium sulfate; or a hormone, such as thyrotropin-releasing hormone.

It must be understood that the use of the particular inducing or enhancing agent is not a part of the present invention per se but is well known to the art. Those of ordinary skill in the art will be well aware of appropriate inducing or enhancing agents. Any such agents which are operable with the parent human peptide hormone-producing cells, when incubated in vitro, may also be used with the hybridoma cells multiplied in a non-human warm-blooded animal in accordance with the present invention.

The human peptide hormone obtained during the in vitro cultivation may be easily collected using conventional purification and separation techniques, such as salting out, dialysis, filtration, centrifugation, concentration and lyopholization. If a further purified human peptide hormone preparation is desirable, a hormone preparation of the highest purity can be obtained by the above mentioned techniques in combination with more sensitive conventional purification and separation techniques, such as adsorption and desorption with ion exchange resin, gel filtration, affinity chromatography, isoelectric point fractionation, electrophoresis, etc.

Occasionally, more than one hormone will be simultaneously produced when the cells obtained and multiplied in accordance with the present invention are cultivated in vitro for hormone production. For example, when the present process is being used for the production of human prolactin, human growth hormone may be produced simultaneously. Similarly, when hACTH is being produced, a large amount of human melanocyte-stimulating hormone (hMSH) and human lipotropin (hLPH) may be produced simultaneously. During hPL production, human chorionic gonadotropin (hCG) can be produced simultaneously. During hTSH production, other human hormones, such as human chorionic gonadotropin and human follicle-stimulating hormone (hFSH) can also be obtained. In all of these cases, the desired hormone can be separated and purified by the known techniques, such as those set forth above. Furthermore, the simultaneously produced hormones may also be separated and purified by similar techniques. The titer of these additional hormones will also be much higher than obtainable by means of the prior art.

The human peptide hormone preparation thus obtained is is advantageously usable alone or in combination with one or more agents for injection, or external, internal, or diagnostic administration in the prevention or treatment of human diseases.

There follow a number of examples of processes in accordance with the present invention for producing human peptide hormones. These examples are intended to be exemplary only and no limitations are intended thereby. In these examples, and elsewhere in the specification, the amount of hormone production is determined by the following procedures. The production of hGH in the culture medium was determined by the radio-immunoassay method as described in S. M. Glick et al, *Nature*, 199, 784 (1963), and expressed by weight in terms of hGH standard preparation distributed by the National Institutes of Health (U.S.A.).

The human insulin in culture medium was determined by the enzyme-immunoassay method as described in K. Kato et al, *J. Biochem.*, 78, 235–237 (1975), and expressed in International Human Insulin Units (IU) wherein 1 IU of human insulin is defined as the amount of insulin that decreases the rabbit blood sugar level to 64 mg/dl within 1 hour, or to 45 mg/dl 2 hours after subcutaneous injection of the insulin preparation.

Human prolactin production is determined by the radioimmunoassay method as described in P. Hang, *Proc. Nat. Acad. Sci. USA*, 68, 1902–1906 (1971), and expressed by weight/ml cell suspension in terms of the NIH standard human prolactin preparation.

The hACTH production was determined by the radioimmunoassay method as described in S. Matsukura et al, *J. Lab. Clin. Med.*, 77, 490–500 (1971), and expressed by weight per ml cell suspension. The hMSH and hLPH productions were determined by the radioimmunoassay method as described in K. Abe et al, *J. Clin. Invest.*, 46, 1906–1916 (1967). First, the total amount of the hormones was determined with human β-MSH standard, then the weight ratio of the hormones was calculated with the amounts of human β-MSH and β-LPH isolated by gel filtration.

The hPL production was determined by the radioimmunoassay method as described in P. Beck et al, *J. Clin. Endocrinol.*, 25, 1457–1462 (1965), and expressed by weight in terms of the standard hPL preparation available from the National Institutes of Health (U.S.A.).

The hCG production was determined by the radioimmunoassay method as described in A. R. Midgley Jr., *Endocrinology*, 79, 10–18 (1966), and expressed in International Units (IU).

The hCT production in the culture medium was determined according to the radio-immunoassay method described in N. A. Samaan et al, *J. Lab. Clin. Med.*, 81, 671–681 (1973), and expressed by weight which is determined with reference to dose-responsive curves obtained with an international reference preparation of calcitonin and available from the World Health Organization.

The hPTH production was determined by the bioassay method as described in J. A. Parsons et al, *Endocrinology*, 92, 454–462 (1973), and expressed by weight in terms of the standard hPTH preparation, assigned 1300 USP units per mg, available from the National Institutes of Health (U.S.A.).

The hTSH production is determined by the radio-receptorassay method as described in S. W. Manley et al, *J. Endocrinol.* 61, 419–436 (1974), and expressed in International Units (IU) in the terms of the standard hTSH preparation available from the National Institute of Medical Research (England). The hFSH production was determined by radioimmunoassay method as described in C. Faiman et al, *J. Clin. Endocrinol. Metab.*, 27, 444–447 (1967) and expressed in International Units (IU).

EXAMPLE 1 hGH Production

A human×human hybridoma lymphoblastoid cell line capable of producing hGH was obtained as follows. First human acidophile adenoma cells were extracted from a patient suffering from acidophile adenoma of the pituitary gland and minced. These disaggregated human acidophile adenoma cells were suspended together with a human Namalva leukemic lymphoblastoid line in a vessel, along with a salt solution containing 140 mM NaCl, 54 mM KCl, 1 mM NaH$_2$PO$_4$ and 2 mM CaCl$_2$. The cells were added in sufficient quantity to give respective cell concentrations of about $10^3$ cells per ml for both types of cells. The ice chilled cell suspension was mixed with a preparation of the same salt solution containing UV-irradiation pre-inactivated Sendai virus, transferred into a 37° C. incubator about five minutes after their mixing and stirred therein for about 30 minutes to effect cell fusion. Obtained hybridoma cells which were found to be capable of producing hGH were cloned according to conventional methods to obtain a human acidophile adenoma×Namalva hybridoma line capable of producing hGH which is usable in accordance with the present invention.

The hybridoma cells so obtained were implanted intraperitoneally into adult nude mice, which were then fed in the usual way for five weeks. The resulting massive tumors, about 15 g each, were disaggregated by extracting, mincing and suspending in a physiological saline solution containing trypsin. After washing the cells with Earle's 199 medium (pH 7.2), supplemented with 10 v/v % fetal bovine serum, the cells were resuspended in a fresh preparation of the same medium which contained 30 mM L-DOPA as the growth hormone inducer and then incubated at 37° C. for six hours to induce hGH. Thereafter, the cells were ultrasonicated, and the hGH content of the supernatant was determined. The hGH production was about 1,800 ng per ml cell suspension.

EXAMPLE 1A hGH (Control)

To compare the hGH production of the hybridoma cells multiplied in vivo as in Example 1 with the hGH production of the hGH-producing parent cells incubated in vitro, the following experiment was conducted. The disaggregated human acidophile adenoma cells obtained by extracting from a patient suffering from acidophile adenoma of the pituitary gland and mincing, were directly cultivated in vitro in Earle's 199 medium (pH 7.2.), supplemented with 10 v/v % fetal bovine serum, and incubated at 37° C. in the presence of 30 mM L-arginine as growth hormone inducer for six hours to induce hGH. Thereafter, the cells were ultra-sonicated and the hGH content of the supernatant was determined. The hGH production was only about 100 ng per ml of suspension.

EXAMPLE 1B hGH (Control)

In order to show the unexpected improvement in hGH production when the hybridoma cells are multiplied in vivo in accordance with the present invention, as compared with the production obtained after in vivo multiplication of the non-hybridoma parent cells, the following control experiment was conducted. Disaggregated human acidophile adenoma cells, obtained by extracting from a patient suffering from acidophile adenoma of the pituitary gland and mincing, were implanted subcutaneously in adult nude mice which were then fed in the usual way for three weeks. The resulting subcutaneously formed massive tumors, about 10 g each, were extracted and treated similarly as in Example 1A to induce and determine the production of hGH. The hGH production was about 500 ng per ml of cell suspension.

EXAMPLE 1C hGH (Control)

This control experiment was conducted in order to compare the amount of hGH produced in accordance with Example 1 with the production obtained from the same hybridoma cells when incubated in vitro without the prior multiplication in vivo. The hybridoma cells obtained in Example 1 were cultivated in vitro in a manner similar to that described in Example 1A using L-DOPA as the growth hormone inducer. The hGH production was only about 100 ng per ml of cell suspension.

EXAMPLE 2 hGH Production

A human×human hybridoma lymphoblastoid line was produced by fusing disaggregated human acidophile adenoma cells with the human JBL leukemic lymphoblastoid line in the manner described in Example 1. The obtained human acidophile adenoma×JBL hybridoma cells were implanted subcutaneously into newborn hamsters, which had previously been injected with antiserum raised in rabbits according to conventional methods, in order to reduce their possible immunoreaction resulting from cell transplantation. The hamsters were fed in the usual way for three weeks. The resulting subcutaneously formed massive tumors, about 10 g each, were extracted and treated as in Example 1WIA to induce hGH. The hGH production was about 1,000 ng per ml of cell suspension.

EXAMPLE 2A hGH (Control)

A control experiment was carried out similarly as in Example 1C by cultivating in vitro the human acidophile adenoma×JBL hybridoma cells obtained in Example 2 and exposing the multiplied cells to growth hormone inducer as in Example 2. The hGH production was only about 200 ng per ml of cell suspension.

EXAMPLE 3 hGH Production

The human acidophile adenoma×Namalva hybridoma cell line obtained in accordance with Example 1 was implanted intravenously into newborn rats. The rats were then fed in the usual way for four weeks. The resulting massive tumors, about 40 g each, were extracted and treated similarly as in Example 2 to induce hGH. The hGH production was about 1,500 ng per ml of cell suspension.

EXAMPLE 3A hGH (Control)

A control experiment was carried out similarly as in Example 1A by cultivating in vitro human acidophile adenoma×Namalva hybridoma cells and exposing the multiplied cells to growth hormone inducer. The hGH production was only about 100 ng pe ml of cell suspension.

EXAMPLE 4 hGH Production

The human acidophile adenoma×JBL hybridoma cell line obtained in accordance with Example 2 was suspended in a physiological saline solution and transferred into a diffusion chamber having an inner volume of about 10 ml and equipped with a membrane filter having a pore size of about 0.5 micron in diameter. The chamber was embedded intraperitoneally into an adult rat. After feeding the rat for four weeks in the usual way, the chamber was removed. The human cell density in the chamber attained by the above operation was about $5\times10^9$ cells per ml, which was about $10^3$-fold or more higher than that obtained by in vitro cultivation using a $CO_2$ incubator. The cells thus obtained were treated similarly as in Example 2 to induce hGH. The hGH production was about 2,200 ng per ml of cell suspension.

EXAMPLE 5 hGH Production

The human acidophile adenoma×JBL hybridoma cell line obtained in accordance with Example 2 was implanted into the allantoic cavities of embryonated eggs which had been preincubated at 37° C. for five days. After incubation of the eggs at this temperature for an additional one week, the multiplied human hybridoma cells were harvested. The cells were treated similarly as in Example 2 to induce hGH. The hGH production was about 1,300 ng per ml cell suspension.

EXAMPLE 6 hGH (Comparison)

The human acidophile adenoma cells obtained similarly as in Example 1A were implanted subcutaneously into adult mice which had previously been irradiated with about 400 rem X-ray irradiation to reduce their immuno-reaction. The mice were fed in the usual way for three weeks. The resulting subcutaneously formed massive tumors, about 15 g each, were extracted and treated similarly as in Example 1 to induce hGH. The hGH production was about 600 ng per ml cell suspension.

EXAMPLE 6A hGH (Control)

A control experiment was carried out similarly as in Example 1A by cultivating in vitro the acidophile adenoma cells and exposing the multiplied cells to the growth hormone inducer of Example 1. The hGH production was only about 200 ng per ml cell suspension.

EXAMPLE 7

Human Insulin Production

A human×human hybridoma lymphoblastoid cell line capable of producing human insulin was obtained in a manner identical to that described for Example 1, except that human insuloma cells, obtained by extraction from an insuloma patient, was substituted for the human acidophile adenoma cells used in example 1. A human insuloma×Namalva hybridoma line capable of producing human insulin was thus produced.

The hybridoma cells so obtained were implanted intraperitoneally into adult nude mice which were then fed in the usual way for five weeks. The resulting massive tumors, about 15 g each, were disaggregated by extracting, mincing and suspending in a physiological saline solution containing collagenase. After washing the cells with Earle's 199 medium (pH 7.2), supplemented with 10 v/v % fetal bovine serum, the cells were resuspended, to give a cell concentration of about $10^5$ cells per ml, in a fresh preparation of the same medium which contained 30 mM L-arginine as the insulin inducer, and then incubated at 37° C. for six hours to induce human insulin. Thereafter, the cells were ultrasonicated, and the human insulin content of the supernatant was determined. The human insulin production was about 3,200 μIU per cell.

EXAMPLE 7A

Human Insulin Control)

To compare the human insulin production of the hybridoma cells multiplied in vivo as in Example 7 with the human insulin production of the human insulin-producing parent cells incubated in vitro, the following experiment was conducted. The disaggregated human insuloma cells obtained by extracting from a patient suffering from insuloma, and then mincing, were directly cultivated in vitro in Earle's 199 medium (pH 7.2.), supplemented with 10 v/v % fetal bovine serum, and incubated at 37° C. in the presence of 20 mM D-glucose as insulin inducer for four hours to induce human insulin. Thereafter, the cells were ultrasonicated and the human insulin content of the supernatant was determined. The human insulin production was only about 200 μIU per cell.

EXAMPLE 7B

Human Insulin (Control)

In order to show the unexpected improvement in human insulin production when the hybridoma cells are multiplied in vivo in accordance with the present invention, as compared with the production obtained after in vivo multiplication of the non-hybridoma parent cells, the following control experiment was conducted. Disaggregated human insuloma cells, obtained by extracting from an insuloma patient and mincing, were implanted subcutaneously in adult nude mice which were then fed in the usual way for three weeks. The resulting subcutaneously formed massive tumors, about 10 g each, were extracted and treated similarly as in Example 7 to induce and determine the production of human insulin, except that 20 mM D-glucose was substituted for the 30 mM of L-arginine as used in Example 7. The human insulin production was about 1,000 μIU per cell.

EXAMPLE 7C

Human Insulin (Control)

This control experiment was conducted in order to compare the amount of human insulin produced in accordance with Example 7 with the production obtained from the same hybridoma cells when incubated in vitro without the prior multiplication in vivo. The human insuloma×Namalva hybridoma Cells obtained in Example 7 were cultivated in vitro in a manner similar to that described in Example 7A using 30 mM L-arginine as the insulin inducer. The human insulin production was only about 100 μIU per cell.

EXAMPLE 7D

Human Insulin (Control)

In order to show the unexpected improvement in human insulin productivity of the human insuloma human leukemic lymphoblastoid hybridoma in accordance with the present invention, as compared with the productivity of human acidophile adenoma human fibroblastoid hybridoma cells capable of producing human insulin, the following control experiments were conducted. Human acidophile adenoma cells were fused with the human HeLa, ATCC CCL 2, cervix epitheloid carcinoma line, similarly as in Example 1. The obtained hybridoma cells capable of producing human insulin were cultured in vitro in a manner similar to that discribed in Example 7C to induce human insulin production. The human insulin production was only about 30 IU per cell.

Separately, the hybridoma cells were implanted intraperitoneally into adult nude mice, and the animals were fed in the usual way for 5 weeks. The resultant massive tumors, about 7 g each, were disaggregated, and cultured in vitro similarly as in Example 7 to induce and determine the human insulin production. The human insulin production so obtained was only about 20 IU per cell.

EXAMPLE 7'

Human Insulin Production

A human human hybridoma lymphoblastoid line was produced by fusing human insuloma cells with the human B-Ta lymphoblastoid line, obtained by transforming normal human lymphocytes with EB virus, in the manner described in Example 1. The human insuloma B-Ta hybridoma cells so obtained were implanted intraperitoneally into adult nude mice, which were then fed in the usual way for five weeks. The resultant massive tumors, about 9 g each, were disaggregated by extracting, mincing and suspending in a physiological saline solution containing collagenase. The multiplied cells were then cultured in vitro similarly as in Example 7 to induce and determine the human insulin production. The human insulin production was about 1900 uIU per cell.

EXAMPLE 8

Human Insulin Production

A human×human hybridoma lymphoblastoid line was produced by fusing disaggregated human insuloma cells with the human JBL leukemic lymphoblasoid line in the manner described above in Example 7. The obtained human insuloma×JBL hybridoma cells were implanted subcutaneously into newborn hamsters, which had previously been injected with antiserum, raised in rabbits according to conventional methods, in order to reduce their possible immunoreaction resulting from cell transplantation. The hamsters were fed in the usual way for three weeks. The resulting subcutaneously formed massive tumors, about 10 g each, were extracted and treated as in Example 1A to induce human insulin. The human insulin production was about 2,300 $\mu$IU per cell.

EXAMPLE 8A

Human Insulin (Control)

A control experiment was carried out similarly as in Example 7C by cultivating in vitro the human insuloma×JBL hybridoma cells obtained in Example 8 and exposing the multiplied cells to insulin inducer as in Example 8. The human insulin production was only about 200 $\mu$IU per cell.

EXAMPLE 9

Human Insulin Production

The human insuloma×Namalva hybridoma cell line obtained in accordance with Example 7 was implanted intravenously into newborn rats. The rats were then fed in the usual way for four weeks. The resulting massive tumors, about 40 g each, were extracted and treated similarly as in Example 2 to induce human insulin. The human insulin production was about 2,600 $\mu$IU per cell.

EXAMPLE 9A

Human Insulin (Control)

A control experiment was carried out similarly as in Example 7A by cultivating in vitro human insuloma×Namalva hybridoma cells and exposing the multiplied cells to insulin inducer as in Example 9. The human insulin production was only about 100 $\mu$IU per cell.

EXAMPLE 10

Human Insulin Production

The human insuloma×JBL hybridoma cell line obtained in accordance with Example 8 was suspended in a physiological saline solution and transferred into a diffusion chamber identical to that of Example 4. The chamber was embedded intraperitoneally into an adult rat. After feeding the rat for four weeks in the usual way, the chamber was removed. The human cell density in the chamber attained by the above operation was about $5\times10^9$ cells per ml, which was about $10^3$-fold or more higher than that obtained by in vitro cultivation using a $CO_2$ incubator. The cells thus obtained were treated similarly as in Example 8 to induce human insulin. The human insulin production was about 2,500 $\mu$IU per cell.

EXAMPLE 11

Human Insulin Production

The human insuloma×JBL hybridoma cell line obtained in accordance with Example 8 was implanted into the allantoic cavities of embryonated eggs which had been preincubated at 37° C. for five days. After incubation of the eggs at this temperature for an additional one week, the multiplied human hybridoma cells were harvested. The cells were treated similarly as in Example 8 to induce human insulin. The human insulin production was about 2,000 $\mu$IU per cell.

EXAMPLE 12

Human Insulin (Comparison)

The human insuloma cells obtained similarly as in Example 1A were implanted subcutaneously into adult mice which had previously been irradiated with about 400 rem X-ray irradiation to reduce their immunoreaction. The mice were fed in the usual way for three weeks. The resulting subcutaneously formed massive tumors, about 15 g each, were extracted and treated similarly as in Example 1B to induce human insulin. The human insulin production was about 1,000 $\mu$IU per cell.

EXAMPLE 13

Human Prolactin Production

A human×human hybridoma lymphoblastoid cell line capable of producing human prolactin was obtained as follows. First, human acidophile adenoma cells were extracted from a patient suffering from acidophile adenoma of the pituitary gland and minced. These disaggregated human acidophile adenoma cells were suspended together with the human Namalva leukemic lymphoblastoid line in a vessel, along with a salt solution containing 140 mM NaCl, 54 mM KCl, 1 mM $NaH_2PO_4$ and 2 mM $CaCl_2$. The cells were added in sufficient quantity to give respective cell concentrations of about $10^3$ cells per ml for both types of cells. The ice chilled cell suspension was mixed with a preparation of the same salt solution containing UV-irradiation preinactivated Sendai virus, transferred into a 37° C. incubator about five minutes after their mixing and stirred therein for about 30 minutes to effect cell fusion. Obtained hybridoma cells which were found to be capable of producing human prolactin were cloned according to conventional methods to obtain a human acidophile adenoma×Namalva hybridoma line capable of producing human prolactin which is usable in accordance with the present invention.

The hybridoma cells so obtained were implanted intraperitoneally into adult nude mice, which were then fed in the usual way for five weeks. The resulting massive tumors, about 15g each, were disaggregated by extracting, mincing and suspending in a physiological saline solution containing trypsin. After washing the cells with Earle's 199 medium (pH 7.2), supplemented with 10 v/v % fetal bovine serum, the cells were resuspended in a fresh preparation of the same medium which contained 10 ng thyrotropin-releasing hormone as the growth hormone inducer and then incubated at 35° C. for six hours to induce human prolactin. Thereafter, the cells were ultrasonicated, and the human prolactin content of the supernatant was determined. The human prolactin production was about 3,300 ng per ml cell suspension.

EXAMPLE 13A

Human Prolactin (Control)

To compare the human prolactin production of the hybridoma cells multiplied in vivo as in Example 13 with the human prolactin production of the human prolactin-producing parent cells incubated in vitro, the following experiment was conducted. The disaggregated human acidophile adenoma cells obtained by extracting from a patient suffering from acidophile adenoma of the pituitary gland and mincing, were directly cultivated in vitro in Earle's 199 medium (pH 7.2.), supplemented with 10 v/v % fetal bovine serum, and incubated at 37° C. for six hours in the presence of 30 mM L-arginine as prolactin inducer to induce human prolactin. Thereafter, the cells were ultra-sonicated and the human prolactin content of the supernatant was determined. The human prolactin production was only about 100 ng per ml of suspension.

EXAMPLE 13B

Human Prolactin (Control)

In order to show the unexpected improvement in human prolactin production when the hybridoma cells are multiplied in vivo in accordance with the present invention, as compared with the production obtained after in vivo multiplication of the non-hybridoma parent cells, the following control experiment was conducted. Disaggregated human acidophile adenoma cells, obtained by extracting from a patient suffering from acidophile adenoma of the pituitary gland and mincing, were implanted subcutaneously in adult nude mice which were then fed in the usual way for three weeks. The resulting subcutaneously formed massive tumors, about 10 g each, were extracted and treated similarly as in Example 13A to induce and determine the production of human prolactin. The human prolactin production was about 600 ng per ml of cell suspension. There was simultaneously produced hGH in an amount of about 500 ng per ml cell suspension.

EXAMPLE 13C

Human Prolactin (Control)

This control experiment was conducted in order to compare the amount of human prolactin produced in accordance with Example 13 with the production obtained from the same hybridoma cells when incubated in vitro without the prior multiplication in vivo. The hybridoma cells obtained in Example 13 were cultivated in vitro in a manner similar to that described in Example 13A, using 10 ng thyrotropin-releasing hormone as the prolactin inducer. The human prolactin production was only about 200 ng per ml of cell suspension.

EXAMPLE 13D

Human Prolactin (Control)

The following control experiments were conducted in order to show the unexpected improvement in human prolactin productivity of the human acidophile adenoma×human leukemic lymphoblastoid hybridoma cells, in accordance with the present invention, as compared with the productivity of human acidophile adenoma×human fibroblastoid hybridoma cells. Human acidophile adenoma cells were fused with the human JT-13 embryonic lung fibroblastoid cell line similarly as in Example 13. The obtained hybridoma cells capable of producing human prolactin were cultured in vitro in a manner similar to that described in Example 13C to induce human prolactin production. The human prolactin production was only about 10 ng per ml of cell suspension.

Separately, the hybridoma cells were implanted intraperitoneally into adult nude mice, which were then fed in the usual way for 5 weeks. The resultant massive tumors, about 10 g each, were disaggregated, and cultured in vitro similarly as in Example 13 to induce and determine human prolactin production. The human prolactin production so obtained was only about 15 ng pe ml of cell suspension.

EXAMPLE 14

Human Prolactin Production

A human×human hybridoma lymphoblastoid line was produced by fusing disaggregated human acidophile adenoma cells with the human JBL leukemic lymphoblasoid line in the manner described in Example 13. The obtained human acidophile adenoma×JBL hybridoma cells were implanted subcutaneously into newborn hamsters, which had previously been injected with antiserum, raised in rabbits according to conventional methods, in order to reduce their possible immunoreaction resulting from cell transplantation. The hamsters were fed in the usual way for three weeks. The resulting subcutaneously formed massive tumors, about 10 g each, were extracted and treated as in Example 13A to induce human prolactin. The human prolactin production was about 1,800 ng per ml cell suspension. The simultaneous hGH production was about 2,000 ng per ml cell suspension.

EXAMPLE 14A

Human Prolactin (Control)

A control experiment was carried out similarly as in Example 13C by cultivating in vitro the human acidophile adenoma×JBL hybridoma cells obtained in Example 14 and exposing the multiplied cells to human prolactin inducer as in Example 14. The human prolactin production was only about 200 ng per ml of cell suspension.

EXAMPLE 15

Human Prolactin Production

The human acidophile adenoma×Namalva hybridoma cell line obtained in accordance with Example 13 was implanted intravenously into newborn rats. The rats were then fed in the usual way for four weeks. The resulting massive tumors, about 40 g each, were extracted and treated similarly as in example 13 to induce human prolactin. The human prolactin production was about 2,700 ng per ml cell suspension.

EXAMPLE 16

Human Prolactin Production

The human acidophile adenoma×JBL hybridoma obtained in accordance with Example 14 was suspended in a physiological saline solution and transferred into a diffusion chamber identical with that of Example 4. The chamber was embedded intraperitoneally into an adult rat. After feeding the rat for four weeks in the usual way, the chamber was removed. The human cell density in the chamber attained by the above operation was about $2 \times 10^9$ cells per ml, which was about $10^3$-fold or more higher than that obtained by in vitro cultivation using a $CO_2$ incubator. The cells thus obtained were treated similarly as in Example 14 to induce human prolactin. The human prolactin production was about 1,900 ng per ml of cell suspension. The simultaneous hGH production was about 2,200 ng per ml cell suspension.

EXAMPLE 16'

Human Prolactin Production

A human×human hybridoma lymphoblastoid line was produced by fusing human acidophile adenoma cells with the human B-Ta lymphoblastoid line, obtained by transforming normal human lymphocytes with EB virus, similarly as in Example 13. The human acidophile adenoma×B-Ta hybridoma cells so obtained were suspended in a physiological saline solution and transferred into a diffusion chamber identical with that of Example 4. The chamber was embedded intraperitoneally into an adult rat. After feeding the rat for four weeks in the usual way, the chamber was removed. The human cell density in the chamber so attained was about $1 \times 10^9$ cells per ml, which was about $10^2$–$10^3$-fold or more higher than that obtained by in vitro culture using a $CO_2$ incubator. The cells thus obtained were treated similarly as in example 14 to induce human prolactin production. The human prolactin production was about 1,200 ng per ml of cell suspension.

EXAMPLE 17

Human Prolactin Production

The human acidophile adenoma×JBL hybridoma cell line obtained in accordance with Example 14 was implanted into the allantoic cavities of embryonated eggs which had been preincubated at 37° C. for five days. After incubation of the eggs at this temperature for an additional one week, the multiplied human hybridoma cells were harvested. The cells were treated similarly as in Example 13 to induce human prolactin. The human prolactin production was about 1,700 ng per ml cell suspension.

EXAMPLE 17A

Human Prolactin (Control)

A control experiment was carried out similarly as in Example 13C by cultivating in vitro human acidophile adenoma×JBL hybridoma cells and exposing the multiplied cells to prolactin inducer as in Example 17. The human prolactin production was only about 200 ng per ml cell suspension.

EXAMPLE 18

Human Prolactin (Comparison)

The human acidophile adenoma cells obtained similarly as in Example 13A were implanted subcutaneously into adult mice which had previously been irradiated with about 400 rem x-ray irradiation to reduce their immunoreaction. The mice were fed in the usual way for three weeks. The resulting subcutaneously formed massive tumors, about 15 g each, were extracted and treated similarly as in Example 13 to induce human prolactin. The human prolactin production was about 800 ng per ml cell suspension.

EXAMPLE 18A

Human Prolactin (Control)

A control experiment was carried out similarly as in Example 13A by cultivating in vitro the acidophile adenoma cells and exposing the multiplied cells to the growth hormone inducer of Example 13. The human prolactin production was only about 200 ng per ml cell suspension.

EXAMPLE 19 hACTH Production

A human×human hybridoma lymphoblastoid cell line capable of producing hACTH was obtained as follows. First, human lung carcinoma cells were extracted from a patient suffering from lung carcinoma and minced. These disaggregated human lung carcinoma cells were suspended together with the human Namalva leukemic lymphoblastoid line in a vessel, along with a salt solution containing 140 mM NaCl, 54 mM KCl, 1 mM $NaH_2PO_4$ and 2 mM $CaCl_2$. The cells were added in sufficient quantity to give respective cell concentrations of about $10^4$ cells per ml for each type of cell. The ice chilled cell suspension was mixed with a preparation of the same salt solution containing UV-irradiation pre-inactivated Sendai virus, transferred into a 37° C. incubator about five minutes after their mixing and stirred therein for about 30 minutes to effect cell fusion. Obtained hybridoma cells which were found to produce hACTH were cloned according to conventional methods to obtain a human lung carcinoma×Namalva hybridoma line capable of producing hACTH which is usable in accordance with the present invention.

The hybridoma cells so obtained were implanted in adult nude mice, which were then fed in the usual way for five weeks. The resulting subcutaneously formed massive tumors, about 15g each, were extracted and disaggregated by mincing and suspended in a physiological saline solution containing trypsin. After washing the cells with Earle's 199 medium (pH 7.2), supplemented with 10 v/v % fetal calf serum, the cells were resuspended in a fresh preparation of the same medium which contained 0.1 µg glucagon per ml as hACTH inducer to give a cell concentration of about $10^6$ cells per ml, and then incubated at 35° C. for twenty hours to induce hormones. Thereafter, the cells were ultrasonicated, and the hACTH, hMSH and hLPH content in the supernatant was determined. The hACTH production was 250 µg per ml cell suspension; hMSH 580 µg per ml; and hLPH, 40 µg per ml.

EXAMPLE 19A hACTH (Control)

In order to show the unexpected improvement in hACTH production when the hybridoma cells are multiplied in vivo in accordance with the present invention, as compared with the production obtained after in vivo multiplication of the nonhybridoma parent cells, the following control experiment was conducted. The disaggregated human lung carcinoma cells, obtained by extracting from a patient suffering from lung carcinoma and mincing, were implanted in adult nude mice which were then fed in the usual way for five weeks. The resulting subcutaneously formed massive tumors, about 5 g each, were extracted and treated similarly as in Example 19 to induce and determine the production of hormones. The hACTH production was only 600 ng per ml cell suspension; hMSH, 1.2 μg per ml; and hLPH, 350 ng per ml.

EXAMPLE 19B hACTH (Control)

In order to show the unexpected improvement in hACTH production with the human lung carcinoma-×human leukemic lymphoblastoid hybridoma in accordance with the present invention, as compared to the production using human lung carcinoma×human fibroblastoid hybridoma cells capable of producing hATCH, the following control experiments were conducted. The human lung carcinoma cells were fused with the human JT-13 embryonic lung fibroblastoid cell line in a manner similar to that described in Example 19. The obtained hybridoma cells capable of producing hATCH were cultured in vitro in a manner similar to that described in Example 19 to induce hATCH production. The hACTH production was only about 400 ng per ml of cell suspension; hMSG, 0.5 μg per ml; and hPL, 200 ng per ml.

Separately the hybridoma cells were implanted into adult nude mice, which were then fed in the usual way for 5 weeks. The resultant massive tumors, about 3 g each, were disaggregated, and cultured in vitro, similarly as in Example 19 to induce and to determine hATCH production. The hACTH production so obtained was only about 600 ng per ml of cell suspension; hMSH, 06 μg per ml; and hPL, 300 ng per ml.

EXAMPLE 19' hACTH Production

A human×human hybridoma lymphoblastoid line was produced by fusing human lung carcinoma cells with the human Q-Ta lymphoblastoid line, obtained by transforming normal human lymphocytes with EB virus, similarly as in Example 19. The obtained human lung carcinoma×Q-Ta hybridoma cells capable of producing hACTH were implanted into the allantoic cavities of embryonated eggs which had been preincubated at 37° C. for five days. After incubation of the eggs at this temperature for an additional week, the multiplied human hybridoma cells were harvested. The cells were treated similarly as in Example 20 to induce hATCH production. The hACTH production was 150 μg per ml of cell suspension.

EXAMPLE 20 hACTH Production

A human×human hybridoma lymphoblastoid line was produced by fusing human chromophobe adenoma cells, obtained by extracting from a patient suffering from chromophobe adenoma of the pituitary gland and mincing, with the human JBL leukemic lymphoblastoid line in the manner described above in Example 19. The obtained human chromophobe adenoma×JBL hybridoma cells were implanted subcutaneously into newborn hamsters, which had previously been injected with antiserum, raised in rabbits according to conventional methods, in order to reduce their possible immunoreaction resulting from cell transplantation. The hamsters were fed in the usual way for three weeks, after which the resulting subcutaneously formed massive tumors, about 10 g each, were extracted and disaggregated by mincing and suspending in a physiological saline solution containing collagenase. After washing the cells with Eagle's minimal essential medium (pH 7.2), supplemented with 5 v/v % human serum, the cells were resuspended to give a cell concentration of about $10^5$ cells per ml and a fresh preparation of the same medium containing 3 μU vasopressin per ml as the inducer, and incubated at 37° C. for 15 hours to induce hormones. The human hormone productions were determined similarly as in Example 19. The hACTH production was 380 μg per ml cell suspension; hMSH, 740 μg per ml; and hLPH, 510 μg per ml.

EXAMPLE 20A hACTH (Control)

A control experiment was carried out by implanting the human chromophobe adenoma cells obtained as in Example 20, in newborn hamsters which had been subjected to immunosuppresion as in Example 20, feeding the animals in the usual way for three weeks, extracting the resulting subcutaneously formed massive tumors, about 3 g each, and disaggregating the massive tumors. The cells so obtained were treated similarly as in Example 20 to induce hormones. The hACTH production was only 750 ng per ml cell suspension; hMSH, 560 ng per ml; and hLPH, 430 ng per ml.

EXAMPLE 21 hACTH Production

A human×human hybridoma lymphoblastoid line was produced by fusing human lung carcinoma cells with the human BALL-1 leukemic lymphoblastoid line in the manner described in Example 19. The obtained human lung carcinoma×BALL-1 hybridoma cells were implanted intravenously into newborn rats. The rats were then fed in the usual way for four weeks. The resulting massive tumors, about 30 g each, were extracted and disaggregated. After washing the cells with RPMI 1640 medium (pH 7.4), supplemented with 10 v/v % fetal calf serum, the cells were resuspended to give a cell concentration of about $10^7$ cells per ml in a fresh preparation of the same medium which contained 6 mM serotonin as the inducer, and then incubated at 30° C. for about 40 hours to induce hormones. The hACTH production was 730 μg per ml cell suspension; and hMSH, 940 μg per ml.

EXAMPLE 21A hACTH (Control)

A control experiment was carried out by implanting human lung carcinoma cells into newborn rats, feeding the animals in the usual way for four weeks extracting the resulting massive tumors, about 5 g each, and disaggregating the massive tumors. The cells obtained were treated similarly as in Example 21. The hACTH production was only 650 ng per ml cell suspension, and hMSH, 1.8 μg per ml.

EXAMPLE 22 hACTH Production

A human×human hybridoma lymphoblastoid line was produced by fusing human chromophobe adenoma cells with the human NALL-1 leukemic lymphoblastoid line in the manner described above in Example 19.

The obtained human chromophobe adenoma×NALL-1 hybridoma cells were implanted subcutaneously into adult mice which had previously been irradiated with about 400 rem X-ray irradiation to reduce their immunoreaction. The mice were fed in the usual way for three weeks. The resulting subcutaneously formed massive tumors, about 15 g each, were extracted and disaggregated. The cells were treated similarly a in Example 20 to induce hormones. The hACTH production was 490 μg per ml cell suspension; and hLPH, 350 μg per ml.

EXAMPLE 22A hACTH (Control)

A control experiment was carried out by implanting the human chromophobe adenoma cells in the irradiated mice, feeding the animals in the usual way for three weeks, extracting the resulting massive tumors, about 5 g each, and disaggregating the massive tumors. The cells obtained were treated similarly as in Example 22. The hACTH production was only 520 ng per ml cell suspension, and hLPH production was only 790 ng per ml.

EXAMPLE 23 hACTH Production

A human×human hybridoma lymphoblastoid line was produced by fusing human lung carcinoma cells with the human TALL-1 leukemic lymphoblastoid line in the manner described above in Example 19. The obtained human lung carcinoma×TALL1 hybridoma cells were suspended in a physiological saline solution and transferred into a diffusion chamber identical to that described in Example 4. The chamber was embedded intraperitoneally in an adult rat and after feeding the animal in the usual way for four weeks, the chamber was removed. The human cell density in the chamber attained by the above operation was about $7 \times 10^8$ cells per ml which was $10^2$-fold or more higher than that attained by in vitro cultivation using a $CO_2$ incubator. The human cells thus obtained were treated similarly as in Example 21 to induce hormones. The hACTH production was 280 μg per ml cell suspension; hMSH, 770 μg per ml; and hLPH, 160 μg per ml.

EXAMPLE 23A hACTH (control)

A control experiment was carried out by suspending human lung carcinoma cells in physiological saline solution, transferring the resulting cell suspension into a plastic cylindrical diffusion chamber, as in Example 23, and harvesting the multiplied human cells after having been embedded intraperitoneally in an adult rat fed in the usual way for four weeks. The harvested human cells (about $10^7$ cells per ml), were treated similarly as in Example 23. The hACTH production was only 480 ng per ml cell suspension; hMSH, 2.3 μg per ml; and hLPH, 250 ng per ml.

EXAMPLE 24 hACTH Production

A human×human hybridoma lymphoblastoid line was produced by fusing human lung carcinoma cells with the human JBL leukemic lymphoblastoid line in the manner described above in Example 19. The obtained human lung carcinoma×JBL hybridoma cells were implanted into the allantoic cavities of embryonated eggs which had been pre-incubated at 37° C. for five days. After incubation of the eggs at this temperature for an additional one week, the multiplied human hybridoma cells were harvested. The cells were treated similarly as in Example 20 to induce hACTH. The hACTH production was 520 μg per ml cell suspension.

EXAMPLE 24A hACTH (Control)

A control experiment was attempted by implanting lung carcinoma cells in the allantoic cavities of embryonated eggs. No cell multiplication was noted.

EXAMPLE 25 hPL Production

A human×human hybridoma lymphoblastoid cell line capable of producing hPL was obtained as follows. First, human chorionic epithelioma cells were extracted from a patient suffering from chorionic epithelioma and minced. These disaggregated human chorionic epithelioma cells were suspended together with the human Namalva leukemic lymphoblastoid line in a vessel, along with a salt solution containing 140 mM NaCl, 54 mM KCl, 1 mM $NaH_2PO_4$ and 2 mM $CaCl_2$. The cells were added in sufficient quantity to give respective cell concentrations of about $10^4$ cells per ml for the two types of cells. The ice chilled cell suspension was mixed with a preparation of the same salt solution containing UV-irradiation preinactivated Sendai virus, transferred into a 37° C. incubator about five minutes after their mixing and stirred therein for about 30 minutes to effect cell fusion. Obtained hybridoma cells which were found to produce hPL were cloned according to conventional methods to obtain a human chorionic epithelioma×Namalva hybridoma line Capable of producing hPL which is usable in accordance with the present invention.

The hybridoma cells so obtained were implanted intraperitoneally into adult nude mice, which were then fed in the usual way for five weeks. The resulting subcutaneously formed massive tumors, about 15g each, were disaggregated by extracting, mincing and suspending in a physiological saline solution containin trypsin. After washing the cells with Earle's 199 medium pH 7.2), supplemented with 10 v/v % fetal calf serum, the cells were resuspended to give a cell concentration of about $10^6$ cells per ml in a fresh preparation of the same medium which contained 30 mM L-arginine as a hormone production enhancing agent, and then incubated at 35° C. for twenty hours to produce hPL. Thereafter, the cells were ultrasonicated, and the hPL content of the resulting supernatant was determined. The hPL production was about 340 μg per ml cell suspension. The simultaneocs hCG production was about 230 IU per ml cell suspension.

EXAMPLE 25A hPL (Control)

This control experiment was conducted in order to compare the amount of hPL produced in accordance with Example 25 with the amount produced after similar in vivo multiplication of the non-hybridoma parent cells. The disaggregated human chorionic epithelioma cells, obtained in the manner described in Example 25, were implanted subcutaneously in adult nude mice which were then fed in the usual way for five weeks.

The resulting subcutaneously formed massive tumors, about 5 g each, were extracted and disaggregated, and then treated similarly as in Example 25 to induce hPL. The hPL production was only 3 µg per ml cell suspension.

EXAMPLE 25B hPL (Control)

The following control experiments were conducted to compare the hPL productivity of the human chorionic epithelioma × human leukemic lymphoblastoid hybridoma cells in accordance with the present invention, with the productivity of human chorionic epithelioma × human fibroblastoid hybrid cells. The fibroblastoid hybridoma cells capable of producing hPL were obtained by fusing human chorionic epithemioma cells with the human JT-13 embryonic lung fibroblastoid cell line, similarly as in Example 25. The hybridoma cells were cultured in vitro in a manner similar to that described in Example 25 to produce hPL. The hPL production was only about 10 ng per ml of cell suspension.

Separately, the hybridoma cells were implanted intraperitoneally into adult nude mice, which were then fed in the usual way for 5 weeks. The resultant massive tumors, about 4 g each, were disaggregated, and cultured in vitro similarly as in Example 25 to produce hPL. The hPL production so obtained was only about 20 ng per ml of cell suspension.

EXAMPLE 26 hPL Production

A human × human hybridoma lymphoblastoid line was produced by fusing disaggregated human lung carcinoma cells, with the human JBL leukemic lymphoblastoid line in the manner described above in Example 29. The obtained human lung carcinoma × JBL hybridoma cells were implanted subcutaneously into newborn hamsters, which had previously been injected with antiserum, raised in rabbits according to conventional methods, in order to reduce their possible immunoreaction resulting from cell transplantation. The hamsters were fed in the usual way for three weeks, after which the resulting subcutaneously formed massive tumors, about 10 g each, were extracted and disaggregated by mincing and suspending in a physiological saline solution containing collagenase. After washing the cells with Eagle's minimal essential medium (pH 7.2), supplemented with 5 v/v % human serum, the cells were resuspended to give a cell concentration of about $10^5$ cells per ml and a fresh preparation of the same medium which contained 20 mM L-lysine and 10 mM magnesium sulfate, and then incubated at 37° C. for 15 hours to produce hPL. The hPL production was about 150 µg per ml cell suspension.

EXAMPLE 26A hPL (Control)

A control experiment was carried out by implanting the human lung carcinoma cells into hamsters similar to those reported in Example 26, feeding the animals in the usual way for three weeks, extracting the resulting subcutaneously formed massive tumors, about 3 g each, and disaggregating the massive tumors. The obtained cells were treated similarly as in Example 26 to produce hPL. The hPL production was only about 0.9 µg per ml cell suspension.

EXAMPLE 27 hPL Production

A human × human hybridoma lymphoblastoid line was produced by fusing disaggregated human chorionic epithelioma cells with the human BALL-1 leukemic lymphoblastoid line in the manner described in Example 25. The obtained human chorionic epithelioma × BALL-1 hybridoma cells were implanted intravenously into newborn rats. The rats were then fed in the usual way for four weeks after which the resulting massive tumor, about 30 g each, were extracted and disaggregated. After washing the cells with RPMI 6040 medium (pH 7.4), supplemented with 10 v/v % fetal calf serum, the cells were resuspended to give a cell concentration of about $10^7$ cells per ml in a fresh preparation of the same medium which contained 30mM L-arginine, and then incubated at 30° C. for about 40 hours to produce hPL. The hPL production was about 410 µg per ml cell suspension. The simultaneous hCG production was about 870 IU per ml cell suspension.

EXAMPLE 27A hPL (Control)

A control experiment was carried out by implanting human chorionic epithelioma cells into newborn rats, feeding the animals in the usual way for four weeks, extracting the resulting massive tumors, about 5 g each, and disaggregating the massive tumors. The cells obtained were treated similarly as in Example 27 to produce hPL. The hPL production was only 2 µg per ml cell suspension.

EXAMPLE 27 hPL Production

A human × human hybridoma lymphoblastoid line was produced by fusing disaggregated human chorionic epithelioma cells with the normal human B-Ta lymphoblastoid line, obtained by transforming normal human lymphocytes with EB virus, in the manner described in Example 25. The obtained hybridoma cells were implanted intravenously into newborn rats. The rats were then fed in the usual way for four weeks after which the resulting massive tumors, about 22 g each, were extracted and disaggregated. The cells obtained were treated similarly as in Example 27 to produce hPL. The hPL production was about 100 µg per ml of cell suspension.

EXAMPLE 28 hPL Production

A human × human hybridoma lymphoblastoid line was produced by fusing human lung carcinoma cells with the human NALL-1 leukemic lymphoblastoid line in the manner described above in Example 25. The obtained human lung carcinoma × NALL-1 hybridoma cells were implanted subcutaneously into adult mice which had previously been irradiated with about 400 rem X-ray irradiation to reduce their immunoreaction. The mice were fed in the usual way for three weeks, after which the resulting subcutaneously formed massive tumors, about 15 g each, were extracted and disaggregated. The obtained cells were treated similarly as in Example 26 to produce hPL. The hPL production was 210 ug per ml cell suspension.

EXAMPLE 28A hPL (Control)

A control experiment was carried out by implanting the human lung carcinoma cells in mice treated as in Example 28, feeding the animals in the usual way for three weeks, extracting the resulting massive tumors, about 5 g each, and disaggregating the massive tumors. The cells obtained were treated similarly as in Example 28 to produce hPL. The hPL production was only 1 μg per ml cell suspension.

EXAMPLE 29 hPL Production

A human×human hybridoma lymphoblastoid line was produced by fusing disaggregated chorionic epithelioma with the human TALL-1 leukemic lymphoblastoid line in the manner described above in Example 25. The obtained human chorionic epithelioma×TALL-1 hybridoma cells were suspended in a physiological saline solution and transferred into a diffusion chamber identical to that described in Example 4. The chamber was embedded intraperitoneally into an adult rat. After feeding the rat in the usual way for four weeks, the chamber was removed. The human cell density in the chamber attained by the above operation was about $7 \times 10^8$ cells per ml which was about $10^2$-fold or more higher than that attained by in vitro cultivation using a $CO_2$ incubator. The hybridoma cells thus obtained were treated similarly as in Example 27 to produce hPL. The hPL production was 380 μg per ml cell suspension. The simultaneous hCG production was about 750 IU per ml cell suspension.

EXAMPLE 29A hPL (control)

A control experiment was carried out by suspending the human chorionic epithelioma cells in physiological saline solution, transferring the resulting cell suspension into a diffusion chamber, as in Example 29, and embedding the chamber intraperitoneally into adult rats, feeding the animals in the usual way for four weeks, and harvesting the multiplied human hybridoma cells (cell density about $10^7$ cells per ml). The obtained cells were treated similarly as in Example 29 to produce hPL. The hPL production was only 1 ug per ml cell suspension.

EXAMPLE 30 hPL Production

A human×human hybridoma lymphoblastoid line was produced by fusing human syncytiotrophoblast cells from chorionic villi with the human JBL leukemic lymphoblastoid line in the manner described above in Exmaple 25. The obtained human syncytiotrophoblast×JBL hybridoma cells were implanted into the allantoic cavities of embryonated eggs which had been pre-incubated at 37° C. for five days. After incubation of the eggs at this temperature for an additional one week, the multiplied human hybridoma cells were harvested. The cells were treated similarly as in Example 25 to induce hPL. The hPL production was 190 μg per ml cell suspension. The simultaneous hCG production was about 210 IU per ml cell suspension.

EXAMPLE 30A hPL (Control)

In a control experiment in which the human syncytiotrophoblast cells were implanted in the allantoic cavities of embryonated eggs, no cell multiplication was noted.

EXAMPLE 31 hCT Production

A human×human hybridoma lymphoblastoid cell line capable of producing human calcitonin was obtained as follows. First, human thyrophyma cells were extracted from a thyrophyma patient and minced. These disaggregated human thyrophyma cells were suspended together with the human Namalva leukemic lymphoblastoid cell line in a vessel, along with a salt solution containing 140 mM NaCl, 54 mM KCl, 1 mM $NaH_2PO_4$ and 2 mM $CaCl_2$. The cells were added in sufficient quantity to give respective cell concentrations of about $10^4$ cells per ml for both types of cells. The ice chilled cell suspension was mixed with a preparation of the same salt solution containing UV-irradiation pre-inactivated Sendai virus, transferred into a 37° C. incubator about five minutes after their mixing and stirred therein for about 30 minutes to effect cell fusion. Obtained hybridoma cells which were found to produce hCT were cloned according to conventional methods to obtain a human thyrophyma×Namalva hybridoma line capable of producing hCT which is usable in accordance with the present invention.

The hybridoma cells so obtained were implanted intraperitoneally into adult nude mice, which were then fed in the usual way for five weeks. The resulting massive tumors, about 15g each, were disaggregated by extracting, mincing and suspending in a physiological saline solution containing trypsin. After washing the cells with Earle's 199 medium (pH 7.2), supplemented with 10 v/v % fetal calf serum, the cells were resuspended to give a cell concentration of about $10^5$ cells per ml in a fresh preparation of the same medium which contained 20 mM $CaCl_2$ and 30 mM L-arginine, and then incubated at 35° C. for forty hours to produce hCT. After the incubation period, the suspension was treated ultrasonically, and the hCT content of the resulting supernatant was determined. The hCT production was about 4.4 μg per ml of the suspension.

EXAMPLE 31A hCT (Control)

To compare the hCT production of the hybridoma cells multiplied in vivo as in Example 31 with the hCT production of the hCT-producing parent cells incubated in vitro, the following experiment was conducted. The disaggregated human thyrophyma cells were directly cultivated in vitro in Earle's 199 medium (pH 7.2), were supplemented with 10 v/v % fetal bovine serum and incubated at 37° C. These cells were treated similarly as in Example 31 to produce hCT. The hCT production was only 10 ng per ml cell suspension.

EXAMPLE 32 hCT Production

A human×human hybridoma lymphoblastoid line was produced by fusing disaggregated and minced human carcinoid cells, extracted from a patient with argentaffinoma of the bronchus with the human JBL leukemic lymphoblastoid line in the manner described above in Example 31. The obtained human carcinoid×JBL hybridoma cells were implanted subcutaneously into newborn hamsters, which had previously been injected with antiserum, raised in rabbits according to conventional methods, in order to reduce their possible immunoreaction resulting from cell transplantation. The hamsters were fed in the usual way for three weeks, after which the resulting subcutaneously formed massive tumors, about 10 g each, were extracted, minced and then suspended in a saline solution containing collagenase to disaggregate the massive tumor. After the disaggregated hybridoma cells were washed with Eagle's minimal essential medium (pH 7.4), containing 5 v/v % human serum, the cell suspension was resuspended in a fresh preparation of the same medium which contained 10 mM $CaCl_2$, 40 mM $MgSO_4$ and 0.1 mM dibutylcyclic AMP to give a cell concentration of about $10^6$ per ml, and then incubated at 37° C. for 30 hours to release hCT. The hCT production was about 3.7 μg per ml cell suspension.

EXAMPLE 32A hCT (Control)

A control experiment was carried out by cultivating in vitro the human carcinoid×JBL hybridoma cells obtained in Example 32 and allowing the multiplied cells to release hCT. The hCT production was only about 60 ng per ml cell suspension

EXAMPLE 33 hCT Production

A human×human hybridoma lymphoblastoid line was produced by fusing human thyrophyma cells with the human BALL-1 leukemic lymphoblastoid line in the manner described in Example 31. The obtained human thyrophyma×BALL-1 hybridoma cells were implanted intravenously into newborn rats. The rats were then fed in the usual way for four weeks after which the resulting massive tumors, about 30 g each, were extracted and treated similarly as in Example 31 to release hCT. The hCT production was about 4.1 μg per ml of the suspension.

EXAMPLE 33A hCT (Control)

A control experiment was carried out similarly as in Example 31A by cultivating in vitro the human thyrophyma×BALL-1 hybridoma cell line and allowing the multiplied cell line to release hCT. The hCT production was only 85 ng per ml cell of the suspension.

EXAMPLE 34 hCT Production

A human×human hybridoma lymphoblastoid line was produced by fusing human lung tumor cells with the human NALL-1 leukemic lymphoblastoid line in the manner described above in Example 31. The obtained human lung tumor×NALL-1 hybridoma cells were implanted subcutaneously into adult mice which had previously been irradiated with about 400 rem X-ray irradiation to reduce their immunoreaction. The mice were fed in the usual way for three weeks, after which the resulting subcutaneously formed massive tumors, about 15 g each, were extracted and tested similarly as in Example 32 to release hTC. The hCT production was 5.2 μg per ml of the suspension.

EXAMPLE 34A hCT (Control)

A control experiment was carried out similarly as in Example 32 by cultivating in vitro the human lung tumor×NALL-1 hybridoma cells and treating the multiplied cells to release hTC. The hCT production was only 90 ng per ml of the suspension.

EXAMPLE 35 hCT Production

A human×human hybridoma lymphoblastoid line was produced by fusing human thyrophyma cells with the human TALL-1 leukemic lymphoblastoid line in the manner described above in Example 31. The obtained human thyrophyma×TALL-1 hybridoma cells were suspended in a physiological saline solution and transferred into a diffusion chamber identical to that described in Example 4. The chamber was embedded intraperitoneally into an adult rat. After feeding the rat in the usual way for four weeks, the chamber was removed. The human cell density in the chamber attained by the above operation was about $7 \times 10^8$ cells per ml which was about $10^2$-fold or more higher than that attained by in vitro cultivation using a $CO_2$ incubator. The cells thus obtained were treated similarly as in Example 32 to produce hCT. The hCT production was 3.1 μg per ml cell suspension.

EXAMPLE 35A hCT (Control)

A control experiment was carried out similarly as in Example 35 by suspending the human thyrophyma cells in a diffusion chamber, which was then embedded into an adult rat, and feeding the rat in the usual way for four weeks. The human cell density thus obtained in this test was about $6 \times 10^6$ cells per ml. The obtained cells were treated similarly as in Example 32 to release hCT. The hCT production was only 15 ng per ml cell suspension.

EXAMPLE 36 hCT Production

A human carcinoid×JBL hybridoma obtained in accordance with Example 32 was implanted into the allantoic cavities of embryonated eggs which had been pre-incubated at 37° C. for five days. After incubation of the eggs at this temperature for an additional one week, the multiplied human hybridoma cells were harvested. The cells were treated similarly as in Example 31 to release hCT. The hCT production was 2.6 μg per ml of the suspension.

EXAMPLE 36A hCT (Control)

Although a control experiment was carried out similarly as in Example 36 by implanting the human carcinoid cells in the allantoic cavities of embryonated eggs, no cell multiplication of the cells was observed therein.

EXAMPLE 37 hPTH Production

A human×human hybridoma lymphoblastoid cell line capable of producing hPTH was obtained as follows. First, human parathyroid tumor cells were extracted from a parathyroid tumor patient and minced. These disaggregated parathyroid tumor cells were suspended together with the human Namalva leukemic lymphoblastoid cell line in a vessel, along with a salt solution containing 140 mM NaCl, 54 mM KCl, 1 mM NaH$_2$PO$_4$ and 2 mM CaCl$_2$, to give respective cell concentrations of about 10$^4$ cells per ml for both types of cells. The ice chilled cell suspension was mixed with a preparation of the same salt solution containing UV-irradiation pre-inactivated Sendai virus, transferred into a 37° C. incubator about five minutes after their mixing and stirred therein for about 30 minutes to effect cell fusion. Obtained hybridoma cells which were found to produce hPTH were cloned according to conventional methods to obtain a human parathyroid tumor×Namalva hybridoma line capable of producing hPTH which is usable in accordance with the present invention.

The hybridoma cells so obtained were implanted intraperitoneally into adult nude mice, which were then fed in the usual way for five weeks. The resulting massive tumors, about 15 g each, were disaggregated by extracting, mincing and suspending in a physiological saline solution containing trypsin. After washing the cells with Earle's 199 medium (pH 7.2), supplemented with 10 v/v % fetal calf serum, the cells were resuspended to give a cell concentration of about 10$^5$ cells per ml in a fresh preparation of the same medium which contained 20 mM CaCl$_2$ and 30 mM L-arginine as hPTH enhancing agents, and then incubated at 37° C. for forty hours to produce hPTH. Thereafter, the cells were ultrasonicated, and the hPTH content of the resulting supernatant was determined. The hPTH production was about 830 ng per ml cell suspension.

EXAMPLE 37A hPTH (Control)

To compare the hPTH production of the hybridoma cells multiplied in vivo as in Example 37 with the hPTH production of the hPTH-producing parent cells incubated in vitro, the following experiment was conducted. The disaggregated human parathyroid tumor cells were directly cultivated in vitro in Earle's 199 medium (pH 7.2), supplemented with 10 v/v % fetal calf serum. These cells were treated similarly as in Example 37 to produce hPTH. The hPTH production was only 4 ng per ml cell suspension.

EXAMPLE 37B hPTH (Control)

In order to compare hPTH productivity of the hPTH producer cell×human lymphoblastoid hybridoma cells in accordance with the present invention, with the productivity of the same hPTH producer cell×human fibroblastoid hybridoma cell, the following control experiments were conducted. Human parathyroid tumor×human fibroblastoid hybridoma cells capable of producing hPTH were obtained by fusing human parathyroid tumor cells with the human JT-13 embryonic lung fibroblastoid cell line, similarly as in Example 37. The hybridoma cells thus obtained were cultured in vitro in a manner similar to that described in Example 37 to produce hPTH. The hPTH production was lower than 1 ng per ml of cell suspension.

Separately, the hybridoma cells were implanted intraperitoneally into adult nude mice, which are then fed in the usual way for 5 weeks. The resultant massive tumors, about 2 g each, were extracted, disaggregated, and cultured in vitro similarly as in Example 3 to produce hPTH. The hPTH production so obtained was only about 2 ng per ml of cell suspension.

EXAMPLE 38 hPTH Production

A human×human hybridoma lymphoblastoid line was produced by fusing disaggregated and minced human kidney carcinoma cells, obtained by extracting from a patient with kidney carcinoma and mincing, with the human JBL leukemic lymphoblastoid line in the manner described above in Example 37. The obtained human kidney carinoma×JBL hybridoma cells were implanted subcutaneously into newborn hamsters, which had previously been injected with antiserum, raised in rabbits according to conventional methods, in order to reduce their possible immunoreaction resulting from cell transplantation. The resulting subcutaneously formed massive tumors, about 10 g each, were extracted and disaggregated by mincing and then suspending in a saline solution containing collagenase. After washing the cells with Eagle's minimal essential medium (pH 7.4), containing 5 v/v % human serum, the cells were resuspended to give a cell concentration of about 10$^6$ cells per ml in a fresh preparation of the same medium which contained 20 mM CaCl$_2$, and 20 mM dopamine, and then incubated at 37° C. for 20 hours to release hPTH The hPTH production was about 1.3 μg per ml cell suspension.

EXAMPLE 38A hPTH (Control)

A control experiment was carried out similarly as in Example 37A by cultivating in vitro the human kidney carcinoma×JBL hybridoma cell line, and then treating the cells as in Example 38. The hPTH production was only about 16 ng per ml cell suspension.

EXAMPLE 39 hPTH Production

A human×human hybridoma lymphoblastoid line was produced by fusing disaggregated human ovarian tumor cells with the human BALL-1 leukemic lymphoblastoid line in the manner described in Example 37. The obtained human ovarian tumor BALL-1 hybridoma cells were implanted intravenously into newborn rats. The rats were then fed in the usual way for four weeks after which the resulting massive tumors, about 30 g each, were extracted and treated similarly as in Example 37 to release hPTH The hPTH production was about 900 ng per ml cell suspension.

EXAMPLE 39A hPTH (Control)

A control experiment was carried out similarly as in Example 37A by cultivating in vitro the human ovarian tumor×BALL-1 hybridoma cells and then treating the cells similarly as in Example 39 to produce hPTH. The hPTH production was only 10 ng per ml cell suspension.

EXAMPLE 40 hPTH Production

A human×human hybridoma lymphoblastoid line was produced by fusing disaggregated human lung carcinoma cells with the human NALL-1 leukemic lymphoblastoid line in the manner described above in Example 37. The obtained human lung carcinoma×NALL-1 hybridoma cells were implanted subcutaneously into adult mice which had previously been irradiated with about 400 rem X-ray irradiation to reduce their immunoreaction. The mice were fed in the usual way for three weeks, after which the resulting subcutaneously formed massive tumors, about 15 g each, were extracted and tested similarly as in Example 38 to release hPTH. The hPTH production was 1.2 μg per ml of the suspension.

EXAMPLE 40A hPTH (Control)

A control experiment was carried out similarly as in Example 37A by cultivating in vitro the human lung carcinoma×NALL-1 hybridoma cells obtained as in Example 40 and treating similarly as in Example 40. The hPTH production was only about 20 ng per ml of the suspension.

EXAMPLE 41 hPTH Production

A human×human hybridoma lymphoblastoid line was produced by fusing disaggregated human parathyroid tumor cells with the human TALL-1 leukemic lymphoblastoid line in the manner described above in Example 37. The obtained human parathyroid tumor×TALL-1 hybridoma cells were suspended in a physiological saline solution and transferred into a diffusion chamber similar to that described in Example 4. The chamber was embedded intraperitoneally into an adult rat. After feeding the rat in the usual way for four weeks, the chamber was removed. The human cell density in the chamber attained by the above operation was about $6 \times 10^8$ cells per ml which was about $10^2$-fold or more higher than that attained by in vitro cultivation using a $CO_2$ incubator. The hybridoma cells thus obtained were treated similarly as in Example 38 to produce hPTH. The hPTH production was 1.1 μg per ml cell suspension.

EXAMPLE 41A hPTH (Control)

To compare the hPTH production of the hybridoma cells multiplied in vivo as in Example 41, with the hPTH production of the parent cells incubated in vitro, the following experiment was conducted. The human parathyroid tumor cells were suspended in physiological saline solution, and the resulting cell suspension was transferred into the diffusion chamber. After embedding the chamber intraperitoneally into an adult rat, the animal was fed in the usual way for four weeks after which the multiplied hybridoma cells were harvested (human cell density about $8 \times 10^6$ cell per ml). The cells were then treated similarly as in Example 41 to produce hPTH. The hPTH production was only about 3 ng per ml cell suspension.

EXAMPLE 42 hPTH Production

A human×human hybridoma lymphoblastoid line was produced by fusing human lung carcinoma cells with the human JBL leukemic lymphoblastoid line in the manner described above in Example 37. The obtained human lung carcinoma×JBL hybridoma cells were implanted into the allantoic cavities of embryonated eggs which had been preincubated at 37° C. for five days. After further incubation of the eggs at this temperature for an additional 1 week, the multiplied human hybridoma cells were harvested. The cells were treated similarly as in Example 37 to produce hPTH. The hPTH production was 700 ng per ml cell suspension.

EXAMPLE 42A hPTH (Control)

In a control experiment in which the human lung carcinoma cells were implanted into the allantoic cavities of embryonated eggs, no cell multiplication of the cells was observed therein.

EXAMPLE 42' hPTH Production

A human×human hybridoma lymphoblastoid line was produced by fusing human parathyroid tumor cells with the human O-Ta lymphoblastoid line, obtained by transforming normal human lymphocytes with EB virus, similarly as in Example 37. The hybridoma cells thus obtained were multiplied in vivo and cultured in vitro in a manner similar to that described in Example 37 to produce hPTH. The hPTH production was about 400 ng per ml of cell suspension.

EXAMPLE 43 hTSH Production

A human×human hybridoma lymphoblastoid cell line capable of producing hTSH was obtained as follows. First, human basophile adenoma cells were extracted from a patient suffering from basophile adenoma of the anterior lobe of the pituitary gland and minced. These disaggregated basophile adenoma cells were suspended together with the human Namalva leukemic lymphoblastoid cell line in a vessel, along with a salt solution containing 140 mM NaCl, 54 mM KCl, 1 mM $NaH_2PO_4$ and 2 mM $CaCl_2$ to give respective cell concentrations of about $10^4$ cells per ml for both types of cells. The ice chilled cell suspension was mixed with a preparation of the same salt solution containing UV-irradiation pre-inactivated Sendai virus, transferred into a 37° C. incubator about five minutes after their mixing and stirred therein for about 30 minutes to effect cell fusion. Obtained hybridoma cells which were found to produce hTSH were cloned according to conventional methods to obtain a human basophile adenoma×Namalva hybridoma line capable of producing hTSH which is usable in accordance with the presen invention.

The hybridoma cells so obtained were implanted intraperitoneally into adult nude mice, which were then fed in the usual way for five weeks. The resulting massive tumors, about 15 g each, were disaggregated by extracting, mincing and suspending in a physiological saline solution containing trypsin. After washing the cells with Earle's 199 medium (pH 7.2), supplemented with 10 v/v % fetal calf serum, the cells were resuspended to give a cell concentration of about 10⁵ cells per ml in a fresh preparation of the same medium which contained 30 mM L-arginine as hTSH enhancing agent, and then incubated at 37° C. for 35 hours to produce hTSH. Thereafter, the cells were ultrasonicated, and the hTSH content of the resulting supernatant was determined. The hTSH production was about 180 mIU per ml cell suspension. Simultaneous hFSH production was about 500 mIU per ml cell suspension.

EXAMPLE 43A hTSH (Control)

To compare the hTSH production of the hybridoma cells multiplied in vivo as in Example 43 with the hTSH production of the hTSH-producing parent cells incubated in vitro, the following experiment was conducted. The disaggregated human basophile adenoma cells were directly cultivated in vitro in Earle's 199 medium (pH 7.2), supplemented with 10 v/v % fetal calf serum. These cells were treated similarly a in Example 43 to produce hTSH. The hTSH production was only 0.3 mIU per ml cell suspension.

EXAMPLE 44 hTSH Production

A human×human hybridoma lymphoblastoid line was produced by fusing disaggregated and minced human chromophobe adenoma cells, obtained by extracting from a patient suffering from chromophobe adenoma of the pituitary gland and mincing, with the human JBL leukemic lymphoblastoid line in the manner described above in Example 43. The obtained human chromophobe adenoma×JBL hybridoma cells were implanted subcutaneously into newborn hamsters, which had previously been injected with antiserum, raised in rabbits according to conventional methods, in order to reduce their possible immunoreaction resulting from cell transplantation. The hamsters were fed in the usual way for three weeks, after which the resulting subcutaneously formed massive tumors, about 10 g each, were extracted and disaggregated by mincing and suspending in a physiological saline solution containing collagenase. After washing the cells with Eagle's minimal essential medium (pH 7.4), supplemented with 5 v/v % human serum, the cells were resuspended to give a cell concentration of about 10⁶ cell per ml in a fresh preparation of the same medium which contained 20 mM L-lysine, 10 mM magnesium sulfate and 10 ng thyrotropin-releasing hormone. The cells were then incubated at 37° C. for 20 hours to produce hTSH. The hTSH production was about 220 mIU per ml cell suspension. The simultaneous hCG production was about 430 IU per ml cell suspension.

EXAMPLE 44A hTSH (Control)

In order to compare the amount of hTSH produced in accordance with Example 44 with the production obtained from the same hybridoma cells when incubated in vitro without the prior multiplication in vivo, the following control experiment was conducted. The human chromophobe adenoma×JBL hybridoma cells were cultivated in vitro in a manner similar to the cultivation of the multiplied cells in Example 44. The hTSH production was only about 8 mIU per ml cell suspension.

EXAMPLE 45 hTSH Production

A human×human hybridoma lymphoblastoid line was produced by fusing human basophile adenoma cells with the human BALL-1 leukemic lymphoblastoid line in the manner described in Example 43. The obtained human basophile adenoma×BALL-1 hybridoma cells were implanted intravenously into newborn rats. The rats were then fed in the usual way for four weeks after which the resulting massive tumors, about 30 g each, were extracted and treated similarly as in Example 43 to release hTSH. The hTSH production was about 160 mIU per ml cell suspension. The simultaneous hTSH production was about 900 mIU per ml cell suspension.

EXAMPLE 45A hTSH (Control)

A control experiment was carried out similarly as in Example 43A by cultivating in vitro the human chromophobe adenoma×BALL-1 hybridoma cells and then treating the cells similarly as in Example 45 to produce hTSH. The hTSH production was only 5 mIU per ml cell suspension.

EXAMPLE 46 hTSH Production

A human×human hybridoma lymphoblastoid line was produced by fusing human chromophobe adenoma cells with the human NALL-1 leukemic lymphoblastoid line in the manner described above in Example 43. The obtained human chromophobe adenoma×NALL-1 hybridoma cells were implanted subcutaneously into adult mice which had previously been irradiated with about 400 rem X-ray irradiation to reduce their immunoreaction. The mice were fed in the usual way for three weeks, after which the resulting subcutaneously formed massive tumors, about 15 g each, were extracted and treated similarly as in Example 44 to release hTSH. The hTSH production was 210 mIU per ml of the suspension. The simultaneous hCG production was about 480 IU per ml cell suspension.

EXAMPLE 46A hTSH (Control)

A control experiment was carried out similarly as in Example 43A by cultivating in vitro the human chromophobe adenoma×NALL-1 hybridoma cells and treating them similarly as in Example 46 to produce hTSH. The hTSH production was only about 7 mIU per ml cell suspension.

EXAMPLE 46B

HTSH (Control)

The following control experiments were conducted to compare the hTSH productivity of the hTSH producer cell×human lymphoblastoid hybridoma cells in accordance with the present invention with the productivity of the same hTSH producer cell after being fused to a human fibroblastoid hybridoma cell. Human chromophobe adenoma cells were fused with the human JT-13 embryonic lung fibroblastoid cell line, similarly as in Example 43. The hybridoma cells thus obtained were cultured in vitro in a manner similar to that described in Example 44 to produce hTSH. The hTSH production was only about 1 mIU per ml of cell suspension.

Separately, the hybridoma cells were implanted subcutaneously into adult mice which had previously received about 400 ram X-ray irradiation to reduce their immunoreaction. The mice were fed in the usual way for three weeks, after which the resulting subcutaneously formed massive tumors, about 4 g each, were extracted and treated similarly as in Example 44 to release hTSH. The hTSH production was 2 mIU per ml of cell suspension.

EXAMPLE 47 hTSH Production

A human×human hybridoma lymphoblastoid line was produced by fusing human basophile adenoma cells with the human TALL-1 leukemic lymphoblastoid line in the manner described above in Example 43. The obtained human basophile adenoma×TALL-1 hybridoma cells were suspended in a physiological saline solution and transferred into a diffusion chamber similar to that described in Example 4. The chamber was embedded intraperitoneally into an adult rat. After feeding the rat in the usual way for four weeks, the chamber was removed. The human cell density in the chamber attained by the above operation was about $7\times 10^8$ cells per ml which was about $10^2$-fold or more higher than that attained by in vitro cultivation using a $CO_2$ incubator. The hybridoma cells thus obtained were treated similarly as in Example 44 to produce hTSH. The hTSH production was 170 mIU per ml cell suspension. The simultaneous hCG production was about 720 IU per ml cell suspension.

EXAMPLE 47A hTSH (Control)

In order to show the unexpected improvement in hTSH production when the hybridoma cells are multiplied in vivo in a diffusion chamber in accordance with the present invention, as compared with that obtained after in vivo multiplication in a diffusion chamber of the non-hybridoma parent cells, the following control experiment was conducted. The human basophile, adenoma cells were suspended in physiological saline solution, and then transferred into the diffusion chamber. The diffusion chamber was embedded intraperitoneally into an adult rat. After feeding the animal in the usual way for four weeks, the multiplied basophile adenoma cells were harvested (cell density about $8\times 10^6$ cell per ml). The cells were then treated similarly as in Example 44 to produce hTSH. The hTSH production was only about 0.1 mIU per ml cell suspension.

EXAMPLE 48 hTSH Production

A human human hybridoma lymphoblastoid line was produced by fusing human lung carcinoma cells with the human JBL leukemic lymphoblastoid line in the manner described above in Example 43. The obtained human lung carcinoma JBL hybridoma cells were implanted into the allantoic cavities of embryonated eggs which had been preincubated at 37° C. for five days. After incubation of the eggs at this temperature for an additional 1 week, the multiplied hybridoma cells were harvested. The cells were treated similarly as in Example 43 to produce hTSH. The hTSH production was 140 mIU per ml cell suspension.

EXAMPLE 48A hTSH (Control)

In a control experiment in which the human lung carcinoma cells were implanted into the allantoic cavities of embryonated eggs, no cell multiplication of the cells was observed.

EXAMPLE 49 hTSH Production

A human×human hybridoma lymphoblastoid line was produced by fusing human chromophobe adenoma cells with the human Q-Ta lymphoblastoid line, obtained by transforming normal lymphocytes with EB virus, similarly as in Example 43. The hybridoma cells thus obtained were multiplied in vivo, and cultured in vitro in a manner similar to that described in Example 46 to produce hTSH. The hTSH production was about 100 mIU per ml of cell suspension.

It will be obvious to those skilled in the art that various changes may be made without departing from the scope of the invention and the invention is not to be considered limited to what is described in the specification.

What is claimed is:

1. In the process for producing human peptide hormone, excluding human erythropoietin, which comprises culturing human cells capable of producing a human peptide hormone on an in vitro nutrient medium under conditions appropriate to accumulate a substantial amount of the human peptide hormone, and recovering the accumulated human peptide hormone from the culture, the improvement, by which the amount of human peptide hormone produced during said in vitro culturing is substantially increased, comprising using as said human cells capable of producing a human peptide hormone, cells obtained by a process comprising:

implanting a human×human hybridoma lymphoblastoid cell line capable of producing said human peptide hormone in a non-human warm-blooded animal;

feeding the animal to allow said human hybridoma cell line to utilize the nutrient body fluid of the animal for its multiplication; and extracting and disaggregating the resultant tumor, formed in the animal, for use in the in vitro production of said human peptide hormone.

2. A process as set forth in claim 1, wherein said human peptide hormone is human insulin.

3. A process as set forth in claim 1, wherein said human peptide hormone is human growth hormone.

4. A process as set forth in claim 1, wherein said human peptide hormone is human prolactin.

5. A process as set forth in claim 1, wherein said human peptide hormone is human adrenocorticotropic hormone.

6. A process as set forth in claim 1, wherein said human peptide hormone is human placental lactogen.

7. A process as set forth in claim 1, wherein said human peptide hormone is human thyroid-stimulating hormone.

8. A process as set forth in claim 1, wherein said human peptide hormone is human parathyroid hormone.

9. A process as set forth in claim 1, wherein said human peptide hormone is human calcitonin.

10. A process as set forth in claim 1, wherein said non-human warm-blooded animal is a fowl or a mammal.

11. A process as set forth in claim 1, wherein said non-human warm-blooded animal is a chicken, pigeon, dog, cat, monkey, goat, pig, cow, horse, rabbit, guinea pig, rat, nude rat, hamster, mouse or nude mouse.

12. A process as set forth in claim 14, wherein said fusing step comprises:
  suspending said parent human cells together with said human lymphoblastoid line in a salt solution containing an effective amount of a cell fusion inducing agent;
  allowing the resultant cell suspension to stand for a period sufficient to effect cell fusion; and
  selecting and cloning a hybridoma line capable of producing human peptide hormone.

13. A process as set forth in claim 12, wherein said cell fusion inducing agent is Sendai virus or polyethylene glycol.

14. A process as set forth in claim 1, wherein said human×human hybridoma lymphoblastoid cell line is obtained by fusing parent human cells inherently capable of producing a human peptide hormone with a human lymphoblastoid line.

15. A process as set forth in claim 14, wherein said parent human cells are normal or tumor human cells.

16. A process as set forth in claim 14, wherein said human peptide hormone is human insulin and said parent human cells are human insuloma cells.

17. A process as set forth in claim 14, wherein said human peptide hormine is human insulin and said parent human cells are human pancreas Langerhans island β-cells.

18. A process as set forth in claim 14, wherein said human peptide hormone is human growth hormone and said parent human cells are human acidophile adenoma cells.

19. A process as set forth in claim 14, wherein said human peptide hormone is humanprolactin and said parent human cells are human acidophile adenoma cells.

20. A process as set forth in claim 14, wherein said human peptide hormone is human adrenocorticotropic hormone and said parent human cells are human chromophobe adenoma cells of the pituitary gland.

21. A process as set forth in claim 2, wherein said human peptide hormone is human placental lactogen and said parent human cells are human chorionic epithelioma cells.

22. A process as set forth in claim 14, wherein said human peptide hormone is humanplacental lactogen and said parent human cells are human syncytiotrophoblast cells from chorionic villi.

23. A process as set forth in claim 14, wherein said human peptide hormone is human thyroid-stimulating hormone and said parent human cells are human basophile adenoma cells.

24. A process as set forth in claim 14, wherein said human peptide hormone is human thyroid-stimulating hormone and said parent human cells are human chromophobe adenoma cells.

25. A process as set forth in claim 14, wherein said human peptide hormone is human parathyroid hormone and said parent human cells are human parathyroid tumor cells.

26. A process as set forth in claim 14, wherein said human peptide hormone is human parathyroid hormone and said parent human cells are human kidney carcinoma cells.

27. A process as set forth in claim 14, wherein said human peptide hormone is human parathyroid hormone and said parent human cells are human ovarian tumor cells.

28. A process as set forth in claim 14, wherein said human peptide hormone is human calcitonin and said parent human cells are human thyrophyma cells.

29. A process as set forth in claim 14, wherein said human peptide hormone is human calcitonin and said parent human cells are human carcinoid cells.

30. A process as set forth in claim 14, wherein said parent human cells are human lung carcinoma cells.

31. A process in accordance with claim 14, wherein said human lymphoblastoid line is of leukemic origin.

32. A process as set forth in claim 14, wherein said human lymphoblastoid line is a member selected from the group of cell lines consisting of Namalva, BALL-1, NALL-1, TALL-1 and JBL.

33. In the process for producing human peptide hormone, excluding human erythropoietin, which comprises culturing human cells capable of producing said peptide hormone on an in vitro nutrient medium under the conditions appropriate to accumulate a substantial amount of the human peptide hormone, and recovering the accumulated human peptide hormone from the culture, the improvement, by which the amount of human peptide hormone produced during said in vitro culturing is substantially increased, comprising using as said human cells capable of producing a human peptide hormone, cells obtained by a process comprising:
  suspending a human×human hybridoma lymphoblastoid cell line capable of producing said human peptide hormone in a device in which the nutrient body fluid of a non-human warm-blooded animal can be supplied to said human hybridoma cell line;
  embedding or placing said device in or on a non-human warm-blooded animal in a manner such that the nutrient body fluid of said animal is supplied to the human hybridoma cell line within said device;
  feeding the animal to allow said human hybridoma cell line to utilize the nutrient body fluid for its multiplication; and
  harvesting the multiplied human hybridoma cells from the device for use in the in vitro production of said human peptide hormone.

34. A process as set forth in claim 33, wherein said human peptide hormone is selected from the group consisting of human insulin, human growth hormone, human prolactin, human adrenocorticotropic hormone, human placental lactogen, human thyroid-stimulating hormone, human parathyroid hormone, and human calcitonin.

35. A process as set forth in claim 33, wherein said device is a diffusion chamber equipped with a membrane filter, ultra-filter or hollow fiber having a nominal pore size in the range of $10^{-7}-10^{-5}$ m.

36. A process as set forth in claim 33, wherein said non-human warm-blooded animal is a fowl or a mammal.

37. A process as set forth in claim 33, wherein said non-human warm-blooded animal is a chicken, pigeon, dog, cat, monkey, goat, pig, cow, horse, rabbit, guinea pig, rat, nude rat, hamster, mouse or nude mouse.

38. A process as set forth in claim 33, wherein said fusing step comprises:
suspending said parent human cells together with said human lymphoblastoid line in a salt solution containing an effective amount of a cell fusion inducing agent;
allowing the resultant cell suspension to stand for a period sufficient to effect cell fusion; and
selecting and cloning a hybridoma line capable of producing human peptide hormone.

39. A process as set forth in claim 38, wherein said cell fusion inducing agent is Sendai virus or polyethylene.

40. A process as set forth in claim 33, wherein said human×human hybridoma lymphoblastoid cell line is obtained by fusing parent human cells inherently capable of producing a human peptide hormone with a human lymphoblastoid line.

41. A process as set forth in claim 40, wherein said parent cells are normal or tumor human cells.

42. A process as set forth in claim 40, wherein said human peptide hormone is human insulin and said parent human cells are human insuloma cells.

43. A process as set forth in claim 40, wherein said human peptide hormine is human insulin and said parent human cells are human pancreas Langerhans island β-cells.

44. A process as set forth in claim 40, wherein said human peptide hormone is human growth hormone and said parent human cells are human acidophile adenoma cells.

45. A process as set forth in claim 40, wherein said human peptide hormone is humanprolactin and said parent human cells are human acidophile adenoma cells.

46. A process as set forth in claim 40, wherein said human peptide hormone is human adrenocorticotropic hormone and said parent human cells are human chromophobe adenoma cells of the pituitary gland.

47. A process as set forth in claim 40, wherein said human peptide hormone is human placental lactogen and said parent human cells are human chorionic epithelioma cells.

48. A process as set forth in claim 40, wherein said human peptide hormone is humanplacental lactogen and said parent human cells are human syncytiotrophoblast cells from chorionic villi.

49. A process as set forth in claim 40, wherein said human peptide hormone is human thyroid-stimulating hormone and said parent human cells are human basophile adenoma cells.

50. A process as set forth in claim 40, wherein said human peptide hormone is human thyroid-stimulating hormone and said parent human cells are human chromophobe adenoma cells.

51. A process as set forth in claim 40, wherein said human peptide hormone is human parathyroid hormone and said parent human cells are human parathyroid tumor cells.

52. A process as set forth in claim 40, wherein said human peptide hormone is human parathyroid hormone and said parent human cells are human kidney carcinoma cells.

53. A process as set forth in claim 40, wherein said human peptide hormone is human parathyroid hormone and said parent human cells are human ovarian tumor cells.

54. A process as set forth in claim 40, wherein said human peptide hormone is human calcitonin and said parent human cells are human thyrophyma cells.

55. A process as set forth in claim 40, wherein said human peptide hormone is human calcitonin and said parent human cells are human carcinoid cells.

56. A process as set forth in claim 40, wherein said parent human cells are human lung carcinoma cells.

57. A process in accordance with claim 40, wherein said human lymphoblastoid line is of leukemic origin.

58. A process as set forth in claim 40, wherein said human lymphoblastoid line is a member selected from the group of cell lines consisting of Namalva, BALL-1, NALL-1, TALL-1 and JBL.

* * * * *